(12) United States Patent
    Stahmann

(10) Patent No.: US 10,716,500 B2
(45) Date of Patent: Jul. 21, 2020

(54) SYSTEMS AND METHODS FOR NORMALIZATION OF CHEMICAL SENSOR DATA BASED ON FLUID STATE CHANGES

(71) Applicant: CARDIAC PACEMAKERS, INC., St. Paul, MN (US)

(72) Inventor: Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 549 days.

(21) Appl. No.: 15/189,400

(22) Filed: Jun. 22, 2016

(65) Prior Publication Data

US 2016/0374597 A1    Dec. 29, 2016

Related U.S. Application Data

(60) Provisional application No. 62/185,958, filed on Jun. 29, 2015.

(51) Int. Cl.
    *A61B 5/1473*    (2006.01)
    *A61B 5/145*     (2006.01)
    (Continued)

(52) U.S. Cl.
    CPC .......... *A61B 5/1473* (2013.01); *A61B 5/0031* (2013.01); *A61B 5/01* (2013.01);
    (Continued)

(58) Field of Classification Search
    CPC ... A61B 5/1473; A61B 5/6861; A61B 5/7221; A61B 5/01; A61B 5/746; A61B 5/14503;
    (Continued)

(56) References Cited

U.S. PATENT DOCUMENTS

| 4,200,110 A | 4/1980 | Peterson et al. |
| 4,321,057 A | 3/1982 | Buckles |
| (Continued) |

FOREIGN PATENT DOCUMENTS

| EP | 2024024 | 2/2009 |
| JP | 57074097 | 5/1982 |
| (Continued) |

OTHER PUBLICATIONS

Arampatzis, S. et al., "Impact of diuretic therapy-associated electrolyte disorders present on admission to the emergency department: a cross-sectional analysis," BMC Medicine 2013, vol. 11, No. 83 (6 pages).

(Continued)

*Primary Examiner* — Eric F Winakur
*Assistant Examiner* — Abid A Mustansir
(74) *Attorney, Agent, or Firm* — Pauly, DeVries Smith & Deffner LLC

(57) ABSTRACT

Embodiments herein include implantable medical systems, devices and methods including chemical sensors. In an embodiment, an implantable medical device system includes a chemical sensor; a fluid state sensor such as a posture sensor; an activity sensor; and/or a respiration sensor. The implantable medical device system can further include normalization circuitry receiving data from the chemical sensor and the fluid state sensor and normalizing the chemical sensor data based on data from the fluid state sensor. In an embodiment, a method of operating an implantable medical device system is included. The method can include measuring the amount of a chemical analyte using a chemical sensor, measuring the fluid status in a patient using a fluid state sensor, and normalizing the measured amount of the chemical analyte as indicated by the chemical sensor using (Continued)

normalization circuitry based on data from the fluid state sensor. Other embodiments are also included herein.

19 Claims, 8 Drawing Sheets

(51) Int. Cl.

| | |
|---|---|
| *A61B 5/00* | (2006.01) |
| *A61N 1/372* | (2006.01) |
| *A61B 5/01* | (2006.01) |
| *A61B 5/05* | (2006.01) |
| *A61B 5/08* | (2006.01) |
| *A61B 5/1459* | (2006.01) |
| *A61B 5/11* | (2006.01) |
| *A61N 1/365* | (2006.01) |
| *A61N 1/36* | (2006.01) |

(52) U.S. Cl.
CPC ............... *A61B 5/05* (2013.01); *A61B 5/08* (2013.01); *A61B 5/1459* (2013.01); *A61B 5/14503* (2013.01); *A61B 5/14532* (2013.01); *A61B 5/14546* (2013.01); *A61B 5/686* (2013.01); *A61B 5/6861* (2013.01); *A61B 5/7221* (2013.01); *A61B 5/746* (2013.01); *A61N 1/37288* (2013.01); *A61B 5/1116* (2013.01); *A61B 5/1118* (2013.01); *A61B 2562/0219* (2013.01); *A61N 1/36* (2013.01); *A61N 1/36557* (2013.01)

(58) Field of Classification Search
CPC ... A61B 5/14532; A61B 5/686; A61B 5/0031; A61B 5/1459; A61B 5/05; A61B 5/08; A61B 5/14546; A61B 5/1118; A61N 1/37288; A61N 1/36; A61N 1/36557
See application file for complete search history.

(56) References Cited

U.S. PATENT DOCUMENTS

| | | |
|---|---|---|
| 4,344,438 A | 8/1982 | Schultz |
| 4,399,099 A | 8/1983 | Buckles |
| 4,680,268 A | 7/1987 | Clark |
| 4,704,029 A | 11/1987 | Van Heuvelen |
| 4,721,677 A | 1/1988 | Clark |
| 4,737,560 A | 4/1988 | Heilmann et al. |
| 4,750,494 A | 6/1988 | King |
| 4,750,495 A | 6/1988 | Moore et al. |
| 4,890,621 A | 1/1990 | Hakky |
| 4,903,701 A | 2/1990 | Moore |
| 4,981,779 A | 1/1991 | Wagner |
| 5,001,054 A | 3/1991 | Wagner |
| 5,096,671 A | 3/1992 | Kane et al. |
| 5,203,348 A | 4/1993 | Dahl et al. |
| 5,209,231 A | 5/1993 | Cote et al. |
| 5,230,337 A | 7/1993 | Dahl et al. |
| 5,267,151 A | 11/1993 | Ham et al. |
| 5,275,171 A | 1/1994 | Barcel |
| 5,312,454 A | 5/1994 | Roline et al. |
| 5,330,718 A | 7/1994 | Hui et al. |
| 5,333,609 A | 8/1994 | Bedingham et al. |
| 5,342,406 A | 8/1994 | Thompson |
| 5,342,789 A | 8/1994 | Chick et al. |
| 5,360,442 A | 11/1994 | Dahl et al. |
| 5,366,496 A | 11/1994 | Dahl et al. |
| 5,378,432 A | 1/1995 | Bankert et al. |
| 5,391,200 A | 2/1995 | Kenknight et al. |
| 5,397,342 A | 3/1995 | Heil et al. |
| 5,457,535 A | 10/1995 | Schmidtke et al. |
| 5,545,202 A | 8/1996 | Dahl et al. |
| 5,553,616 A | 9/1996 | Ham et al. |
| 5,556,421 A | 9/1996 | Prutchi et al. |
| 5,560,356 A | 10/1996 | Peyman |
| 5,603,732 A | 2/1997 | Dahl et al. |
| 5,605,152 A | 2/1997 | Slate et al. |
| 5,728,281 A | 3/1998 | Holmstrom et al. |
| 5,830,138 A | 11/1998 | Wilson |
| 5,854,078 A | 12/1998 | Asher et al. |
| 5,871,442 A | 2/1999 | Madarasz et al. |
| 5,902,326 A | 5/1999 | Lessar et al. |
| 5,916,243 A | 6/1999 | Kenknight et al. |
| 5,958,782 A | 9/1999 | Bentsen et al. |
| 5,958,786 A | 9/1999 | Munkholm |
| 5,995,860 A | 11/1999 | Sun et al. |
| 6,002,954 A | 12/1999 | Van Antwerp et al. |
| 6,011,984 A | 1/2000 | Van Antwerp et al. |
| 6,037,137 A | 3/2000 | Komoriya et al. |
| 6,040,194 A | 3/2000 | Chick et al. |
| 6,049,727 A | 4/2000 | Crothall |
| 6,122,536 A | 9/2000 | Sun et al. |
| 6,125,290 A | 9/2000 | Miesel |
| 6,125,291 A | 9/2000 | Miesel et al. |
| 6,134,459 A | 10/2000 | Roberts et al. |
| 6,144,866 A | 11/2000 | Miesel et al. |
| 6,163,714 A | 12/2000 | Stanley et al. |
| 6,187,599 B1 | 2/2001 | Asher et al. |
| 6,216,022 B1 | 4/2001 | Tyrrell et al. |
| 6,219,137 B1 | 4/2001 | Vo-Dinh |
| 6,232,130 B1 | 5/2001 | Wolf |
| 6,236,870 B1 | 5/2001 | Madarasz et al. |
| 6,239,255 B1 | 5/2001 | Furlong et al. |
| 6,256,522 B1 | 7/2001 | Schultz |
| 6,267,724 B1 | 7/2001 | Taylor et al. |
| 6,268,161 B1 | 7/2001 | Han et al. |
| 6,277,627 B1 | 8/2001 | Hellinga |
| 6,304,766 B1 | 10/2001 | Colvin, Jr. |
| 6,330,464 B1 | 12/2001 | Colvin et al. |
| 6,368,274 B1 | 4/2002 | Van Antwerp et al. |
| 6,383,767 B1 | 5/2002 | Polak |
| 6,438,397 B1 | 8/2002 | Bosquet et al. |
| 6,442,409 B1 | 8/2002 | Peyman |
| 6,454,710 B1 | 9/2002 | Ballerstadt et al. |
| 6,491,639 B1 | 12/2002 | Turcott |
| 6,505,059 B1 | 1/2003 | Kollias et al. |
| 6,521,446 B2 | 2/2003 | Hellinga |
| 6,544,800 B2 | 4/2003 | Asher |
| 6,579,690 B1 | 6/2003 | Bonnecaze et al. |
| 6,594,510 B2 | 7/2003 | Madarasz et al. |
| 6,625,479 B1 | 9/2003 | Weber et al. |
| 6,666,821 B2 | 12/2003 | Keimel et al. |
| 6,671,527 B2 | 12/2003 | Petersson et al. |
| 6,673,596 B1 | 1/2004 | Sayler et al. |
| 6,682,938 B1 | 1/2004 | Satcher, Jr. et al. |
| 6,694,158 B2 | 2/2004 | Polak |
| 6,711,423 B2 | 3/2004 | Colvin |
| 6,731,976 B2 | 5/2004 | Penn et al. |
| RE38,525 E | 6/2004 | Stanley et al. |
| 6,766,183 B2 | 7/2004 | Walsh |
| 6,771,993 B2 | 8/2004 | Rule et al. |
| 6,800,451 B2 | 10/2004 | Danioloff et al. |
| 6,804,544 B2 | 10/2004 | Van Antwerp et al. |
| 6,835,553 B2 | 12/2004 | Han et al. |
| 6,855,556 B2 | 2/2005 | Amiss et al. |
| 6,861,232 B2 | 3/2005 | Schaffar |
| 6,885,881 B2 | 4/2005 | Leonhardt |
| 6,885,883 B2 | 4/2005 | Parris et al. |
| 6,893,545 B2 | 5/2005 | Gotoh et al. |
| 6,918,873 B1 | 7/2005 | Millar et al. |
| 6,928,325 B2 | 8/2005 | Zhu et al. |
| 6,944,488 B2 | 9/2005 | Roberts |
| 6,952,603 B2 | 10/2005 | Gerber et al. |
| 6,957,094 B2 | 10/2005 | Chance et al. |
| 6,978,182 B2 | 12/2005 | Mazar et al. |
| 6,993,389 B2 | 1/2006 | Ding et al. |
| 7,016,714 B2 | 3/2006 | Colvin, Jr. et al. |
| 7,039,446 B2 | 5/2006 | Ruchti et al. |
| 7,107,086 B2 | 9/2006 | Reihl et al. |
| 7,133,710 B2 | 11/2006 | Acosta et al. |
| 7,134,999 B2 | 11/2006 | Brauker et al. |
| 7,164,948 B2 | 1/2007 | Struble et al. |
| 7,228,159 B2 | 6/2007 | Petersson et al. |

(56) References Cited

U.S. PATENT DOCUMENTS

| | | | |
|---|---|---|---|
| 7,248,906 B2 | 7/2007 | Dirac et al. | |
| 7,276,027 B2 | 10/2007 | Haar et al. | |
| 7,277,740 B2 | 10/2007 | Rohleder et al. | |
| 7,373,195 B2 | 5/2008 | Ye | |
| 7,384,396 B2 | 6/2008 | Samuels et al. | |
| 7,435,385 B2 | 10/2008 | Lin et al. | |
| 7,447,533 B1 | 11/2008 | Fang et al. | |
| 7,450,980 B2 | 11/2008 | Kawanishi | |
| 7,473,548 B2 | 1/2009 | Soykan et al. | |
| 7,496,392 B2 | 2/2009 | Alarcon et al. | |
| 7,604,593 B2 | 10/2009 | Parris et al. | |
| 7,629,172 B2 | 12/2009 | Alarcon et al. | |
| 7,787,923 B2 | 8/2010 | Alarcon et al. | |
| 7,800,078 B2 | 9/2010 | Colvin, Jr. et al. | |
| 7,809,441 B2 | 10/2010 | Kane et al. | |
| 7,863,038 B2 | 1/2011 | Motamedi et al. | |
| 7,964,390 B2 | 6/2011 | Rozakis et al. | |
| 8,086,323 B2 | 12/2011 | Reghabi et al. | |
| 8,092,386 B1* | 1/2012 | Wenzel | A61B 5/01 600/316 |
| 8,126,554 B2 | 2/2012 | Kane et al. | |
| 8,129,191 B2 | 3/2012 | Sheard et al. | |
| 8,571,659 B2 | 10/2013 | Kane et al. | |
| 9,213,010 B2 | 12/2015 | Yang et al. | |
| 2002/0016535 A1 | 2/2002 | Martin et al. | |
| 2002/0033454 A1 | 3/2002 | Cheng et al. | |
| 2002/0035317 A1 | 3/2002 | Cheng et al. | |
| 2002/0045272 A1 | 4/2002 | Mcdevitt et al. | |
| 2002/0095075 A1 | 7/2002 | Madarasz et al. | |
| 2002/0127626 A1 | 9/2002 | Daniloff et al. | |
| 2002/0143264 A1 | 10/2002 | Ding et al. | |
| 2003/0100040 A1 | 5/2003 | Bonnecaze et al. | |
| 2003/0125611 A1 | 7/2003 | Bardy | |
| 2003/0171666 A1 | 9/2003 | Loeb et al. | |
| 2003/0191376 A1 | 10/2003 | Samuels et al. | |
| 2003/0208113 A1 | 11/2003 | Mault et al. | |
| 2003/0231294 A1 | 12/2003 | Wariar et al. | |
| 2004/0023317 A1 | 2/2004 | Motamedi et al. | |
| 2004/0030365 A1 | 2/2004 | Rubin | |
| 2004/0059206 A1 | 3/2004 | Braig et al. | |
| 2004/0073100 A1 | 4/2004 | Ballerstadt et al. | |
| 2004/0087842 A1 | 5/2004 | Lakowicz et al. | |
| 2004/0100376 A1 | 5/2004 | Lye et al. | |
| 2004/0122489 A1* | 6/2004 | Mazar | A61N 1/37282 607/60 |
| 2004/0132172 A1 | 7/2004 | Cunningham et al. | |
| 2004/0133079 A1 | 7/2004 | Mazar et al. | |
| 2004/0147034 A1 | 7/2004 | Gore et al. | |
| 2004/0161853 A1 | 8/2004 | Yang et al. | |
| 2004/0180379 A1 | 9/2004 | Van Duyne et al. | |
| 2004/0180391 A1 | 9/2004 | Gratzl et al. | |
| 2004/0186359 A1 | 9/2004 | Beaudoin et al. | |
| 2004/0199062 A1 | 10/2004 | Petersson et al. | |
| 2004/0206916 A1 | 10/2004 | Colvin, Jr. et al. | |
| 2004/0215134 A1 | 10/2004 | Soykan et al. | |
| 2004/0249311 A1 | 12/2004 | Haar et al. | |
| 2004/0254438 A1 | 12/2004 | Chuck et al. | |
| 2004/0260162 A1 | 12/2004 | Rohleder et al. | |
| 2005/0004439 A1* | 1/2005 | Shin | A61B 5/14532 600/365 |
| 2005/0027176 A1 | 2/2005 | Xie | |
| 2005/0033133 A1 | 2/2005 | Kraft | |
| 2005/0038329 A1 | 2/2005 | Morris et al. | |
| 2005/0038332 A1* | 2/2005 | Saidara | A61B 5/0002 600/347 |
| 2005/0042704 A1 | 2/2005 | Alarcon et al. | |
| 2005/0043894 A1 | 2/2005 | Fernandez | |
| 2005/0065464 A1 | 3/2005 | Talbot et al. | |
| 2005/0065556 A1 | 3/2005 | Reghabi et al. | |
| 2005/0070768 A1 | 3/2005 | Zhu et al. | |
| 2005/0070770 A1 | 3/2005 | Dirac et al. | |
| 2005/0070771 A1 | 3/2005 | Rule et al. | |
| 2005/0113657 A1 | 5/2005 | Alarcon et al. | |
| 2005/0113658 A1 | 5/2005 | Jacobson et al. | |
| 2005/0130249 A1 | 6/2005 | Parris et al. | |
| 2005/0137481 A1 | 6/2005 | Sheard et al. | |
| 2005/0137626 A1 | 6/2005 | Pastore et al. | |
| 2005/0148832 A1 | 7/2005 | Reghabi et al. | |
| 2005/0154272 A1 | 7/2005 | Dirac et al. | |
| 2005/0221276 A1 | 10/2005 | Rozakis et al. | |
| 2005/0288721 A1 | 12/2005 | Girouard et al. | |
| 2006/0025748 A1 | 2/2006 | Ye | |
| 2006/0217771 A1 | 9/2006 | Soykan et al. | |
| 2007/0027495 A1 | 2/2007 | Gerber | |
| 2007/0088220 A1 | 4/2007 | Stahmann | |
| 2007/0270674 A1 | 11/2007 | Kane et al. | |
| 2007/0270675 A1 | 11/2007 | Kane et al. | |
| 2008/0214910 A1* | 9/2008 | Buck | G01N 27/3274 600/310 |
| 2009/0069708 A1 | 3/2009 | Hatlestad et al. | |
| 2009/0247891 A1 | 10/2009 | Wood | |
| 2010/0010571 A1* | 1/2010 | Skelton | A61B 5/1116 607/59 |
| 2012/0197231 A1 | 8/2012 | Kane et al. | |
| 2012/0262298 A1* | 10/2012 | Bohm | G01N 27/3274 340/604 |
| 2013/0207889 A1 | 8/2013 | Chang et al. | |
| 2014/0039383 A1* | 2/2014 | Dobbles | G06F 19/00 604/66 |
| 2014/0276164 A1 | 9/2014 | Thakur et al. | |
| 2014/0277280 A1 | 9/2014 | Saha et al. | |
| 2014/0278189 A1* | 9/2014 | Vanslyke | G16H 40/40 702/104 |
| 2015/0038866 A1 | 2/2015 | Zhang et al. | |
| 2015/0126883 A1 | 5/2015 | An et al. | |
| 2016/0073879 A1* | 3/2016 | Mensinger | A61B 5/0004 340/870.07 |

FOREIGN PATENT DOCUMENTS

| | | |
|---|---|---|
| JP | 2005315871 | 11/2005 |
| WO | 9625978 | 8/1996 |
| WO | 9626526 | 8/1996 |
| WO | 9719188 | 5/1997 |
| WO | 9801071 | 1/1998 |
| WO | 200025862 | 5/2000 |
| WO | 200025863 | 5/2000 |
| WO | 200180728 | 11/2001 |
| WO | 2004039265 | 5/2004 |
| WO | 2004071291 | 8/2004 |
| WO | 2004081522 | 9/2004 |
| WO | 2004091719 | 10/2004 |
| WO | 2004092713 | 10/2004 |
| WO | 2005074612 | 8/2005 |
| WO | 2006017169 | 2/2006 |
| WO | 2007137037 | 11/2007 |
| WO | 2008106612 | 9/2008 |
| WO | 2009064773 | 5/2009 |

OTHER PUBLICATIONS

Assubaie, F. N. et al., "Guanidinium Ion-selective Electrodes Based on Dibenzo-27-crown-9 and Tetraphenylborate," Analyst Jan. 1988, vol. 113, 61-64.

Assubaie, Fahad N. et al., "Comparative Study of Polyether-type Neutral Carriers for the Potentiometric Sensing of Guanidinium Ions," Analyst Dec. 1989, vol. 114, 1545-1550.

Baer, Daniel M. et al., "Investigating elevated potassium values," MLO, Nov. 2006 pp. 24-31 (4 pages).

Bakker, Eric et al., "Carrier-Based Ion-Selective Electrodes and Bulk Optodes. 1. General Characteristics," Chem. Rev. 1997, pp. 3083-3132.

Benco, John S. et al., "Optical Sensors for Blood Analytes," The Spectrum, vol. 14, Issue 4 Winter 2001, pp. 4-11.

Bender, J. W. et al., "The Use of Biomedical Sensors to Monitor Capsule Formation Around Soft Tissue Implants," Annals of Plastic Surgery, vol. 56, No. 1 Jan. 2006, pp. 72-75.

Berberich, Jason A. et al., "A stable three-enzyme creatinine biosensor. 1. Impact of structure, function and environment on PEGylated and immobilized sarcosine oxidase," Acta Biomaterialia 2005, 1, 173-181.

(56) References Cited

OTHER PUBLICATIONS

Bielecka-Dabrowa, Agata et al., "The meaning of hypokalemia in heart failure," International Journal of Cardiology 158 (2012) pp. 12-17 (6 pages).
Bochenska, Maria et al., "Sulfonamides as Ionophores for Ise. III. Guanidinium Ion-Selective Electrodes Based on Lipophilic Bis-Sulfonamide," J. Coord. Chem. 1992, vol. 27, pp. 145-149.
Bowling, C. B. et al., "Hypokalemia and Outcomes in Patients With Chronic Heart Failure and Chronic Kidney Disease," Circ Heart Fail (2010), vol. 3, No. 2, pp. 253-260 (9 pages).
Braatz, James A. "Biocompatible Polyurethane-Base Hydrogel," Journal of Biomaterials Application Jul. 1994, vol. 9, pp. 71-96.
Buhlmann, Philippe et al., "Carrier-Based Ion-Selective Electrodes and Bulk Optodes. 2. Ionophores for Potentiometric and Optical Sensors," Chem. Rev. 1998 1998, 1953-1687.
Charles, Paul T. et al., "Fabrication and characterization of 3D hydrogel microarrays to measure antigenicity and antibody functionality for biosensor applications," Biosensors and Bioelectronics 2004, 20, pp. 753-764.
"Communication pursuant to Article 94(3) EPC," for European Patent application No. 07762189.4-2305 dated Mar. 16, 2010 (3 pages).
Drevon, Geraldine F. et al., "High-Activity Enzyme-Polyurethane Coatings," Biotechnology and Bioengineering Sep. 30, 2002, vol. 79, No. 7, pp. 784-794.
"EP Communication," for EP Patent Application No. 07762189.4 dated Mar. 24, 2009 (3 pages).
"EP Response to Communication," for EP Patent Application No. 07762189.4 filed Jul. 27, 2009 (9 pages).
"File History" for U.S. Appl. No. 11/383,933 downloaded Aug. 1, 2016 (1894 pages).
"File History" for U.S. Appl. No. 11/383,926 downloaded Aug. 3, 2016 (1241 pages).
"File History" for U.S. Appl. No. 13/359,591 downloaded Aug. 3, 2016 (427 pages).
"File History" for U.S. Appl. No. 12/269,510 downloaded Aug. 5, 2016 (559 pages).
Garcia, Carlos D. et al., "Direct detection of renal function markers using microchip CE with pulsed electrochemical detection," The Analyst www.rsc.org/analyst May 12, 2004, 1-6.
Gerritsen, Martijn "Problems Associated With Subcutaneously Implanted Glucose Sensors," Diabetes Care Feb. 2000, vol. 23, No. 2, pp. 143-145.
Han, In S. et al., "Constant-vol. Hydrogel Osmometer: A New Device Concept for Miniature Biosensors," Biomacromolecules, 3 2002, pp. 1271-1275.
He, Huarui et al., "Enantioselective Optodes," Analytica Chimica Acta, 246 1991, pp. 251-257.
He, Z. K. et al., "Calibrationless Determination of Creatinine and Ammonia by Coulometric Flow Titration," Analytical Biochemistry 2000, 283, pp. 166-174.
Holtz, John H. et al., "Polymerized colloidal crystal hydrogel films as intelligent chemical sensing materials," Nature Oct. 23, 1997, vol. 389, pp. 829-832.
Hulanicki, Adam et al., "Chemical Sensors Definitions and Classification," Pure & Applied Chemistry, vol. 63, No. 9, pp. 1247-1250, 1991 (4 pages).
"International Preliminary Report on Patentability," for International Application No. PCT/US2008/083218 dated May 18, 2010 (6 pages).
"International Preliminary Report on Patentability," from International Application No. PCT/US2007/068954 dated Nov. 17, 2008 (9 pages).
"International Search Report and Written Opinion," for International Application No. PCT/US2007/068954 dated Nov. 17, 2008 (12 pages).
"Japanese office action Received," from JP Application No. 2009-511204, dated Mar. 27, 2012, (pp. 1-7) Including English translation., 7.
Kataky, Ritu et al., "Local Anesthetics Measured by Lipophilic β-Cyclodextrin-Based-Ion-Selective Electrodes," Electroanalysis 1996, vol. 8, No. 6, pp. 585-590.
Kataky, Ritu et al., "Selective Binding and Sensing of Guanidinium Ions by Lipophilic Cyclodextrins," J. Chem. Soc. Perkin Trans. 2 1994, 2381-2382.
Kelly, Patricia M. et al., "Selective sensing of guanidinium and tetraalkylammonium ions using lipophilic cyclodextrins," J. Chem. Soc. Perkin Trans. 2 1995, pp. 1955-1963.
Killard, Anthony J. et al., "Creatinine biosensors: principles and designs," TIBTECH 2000, vol. 18, pp. 433-437.
Kimble, Kyle W. et al., "Progress toward the development of a point-of-care photonic crystal ammonia sensor," Anal Bioanal Chem 2006, 385: 678-685.
Kremer, Felix J. et al., "Improved Guanidinium Ion-selectivity by Novel Calix(4)arene and Calix(6)arene Receptor Molecules on CHEMFETs," J. Chem. Soc. Perkin Trans. 2 1994, 677-681.
Kuwana, Eddy et al., "Fluorescence Lifetime Spectroscopy of a pH-Sensitive Dye Encapsulated in Hydrogel Beads," Bitechnol. Prog. 2004, 20, pp. 1561-1566.
Kuwana, Eddy et al., "Sensing of pH in Multiply Scattering Media with Fluorescence Lifetime," Advanced Biomedical and Clinical Diagnostic Systems, Proceedings of SPIE, vol. 4958 2003, pp. 32-42.
Lehn, J. M. et al., "[2]-Cryptates: Stability and Selectivity of Alkali and Akaline-Earth Macrobicycle Complexes," Journal of the American Chemical Society Nov. 12, 1975, pp. 6700-6707.
Lejeune, Keith E. et al., "Covalent Binding of a Nerve Agent Hydrolyzing Enzyme Within Polyurethane Foams," Biotechnology and Bioengineering 1996, vol. 51, pp. 450-457.
Lejeune, Keith E. et al., "Dramatically Stabilized Phosphotriesterase-Polymers for Nerve Agent Degradation," Biotechnology and Bioengineering Apr. 20, 1997, vol. 54, No. 2, pp. 105-114.
Li, Hong et al., "An optical biosensor for lysine based on the use of lysine decarboxylase and a cadaverine-sensitive membrane," Biosensors and Bioelectronics 1992, vol. 7, issue 10, pp. 725-732.
Liamis, G. et al., "Electrolyte Disorders in Community Subjects: Prevalence and Risk Factors," The American Journal of Medicine, vol. 126, No. 3, Mar. 2013, pp. 253-260 (8 pages).
Lindinger, J. et al., "K+ and Lac-distribution in humans during and after high-intensity exercise: role in muscle fatigue attenuation?," J. Appl. Physiol. (1995) 78:765-777 (13 pages).
Linton, R.A. F. et al., "Arterial Plasma potassium measured continuously during exercise in man," Clinical Science (1984) 67:427-431 (5 pages).
Marshall, A. J. et al., "Quantitative Characterization of Sphere-Templated Porous Biomaterials," AIChE Journal Apr. 2005, vol. 51, No. 4, pp. 1221-1232.
Martin, Stephanie M. et al., "Characterization and analysis of osteopontin-immobilized poly(2-hydroxyethyl methacrylate) surfaces," Wiley Periodicals, Inc. 2003, 335-343.
Martin, Stephanie M. et al., "Enhancing the biological activity of immobilized osteopontin using a type-1 collagen affinity coating," Wiley Periodicals, Inc. 2004, 10-19.
Medbo, John I. et al., "Plasma Potassium Changes with High Intensity Exercise," Journal of Physiology (1990), 421, pp. 105-122 (18 pages).
Meyerhoff, Mark E. "New In Vitro Analytical Approaches for Clinical Chemistry Measurements in Critical Care," Clin. Chem. 1990, 36/8(B), pp. 1567-1572.
"Microminiature Device Monitors Vital Electrolytes and Metabolites," John Glenn Biomedical Engineering Consortium NASA Glenn Research Center, Cleveland, OH May 2002, 2 pages.
"Microminiature Monitor for Vital Electrolyte and Metabolite Levels of Astronauts—Status Report," John Glenn Biomedical Engineering Consortium NASA Glenn Research Center at Lewis Field, 5 pages.
Muir, William W. et al., "Effects of Acute Hyperventilation on Serum Potassium in the Dog," Veterinary Surgery, 19, 1, 83-87, 1990 (5 pages).
Nishiya, Yoshiaki et al., "Cloning and Sequencing of the Sarcosine Oxidase Gene from *Arthrobacter* sp. TE1826," Journal of Fermentation and Bioengineering 1993, vol. 75, No. 4, pp. 239-244.

(56) References Cited

OTHER PUBLICATIONS

Norris, P. et al., "Ultrasonically Controlled Release of Ciprofloxacin from Self-Assembled Coatings on Poly(2-Hydyoxyethyl Methacrylate) Hydrogels fro Pseudomonas earuginosa Biofilm Prevention," Antimicrobial Agents and Chemotherapy Oct. 2005, vol. 49, No. 10, pp. 4272-4279.
On Ho, Wah et al., "Electrochemical Sensor for Measurement of Urea and Creatinine in Serum Based on ac Impedance Measurement of Enzyme-Catalyzed Polymer Transformation," Anal. Chem. 1999, 71, pp. 1940-1946.
Parker, David et al., "Selectivity in the binding and detection of charge diffuse ions," Pure & Appl. Chem. 1996, vol. 68, No. 6, pp. 1219-1223.
"PCT International Search Report and Written Opinion," for International Application No. PCT/US2007/068954, dated Nov. 17, 2008 (12 pages).
"PCT International Search Report and Written Opinion," for International patent application No. PCT/US2008/083218 dated May 14, 2010 (8 pages).
Hadomska, Anna et al., "Creatinine biosensor based on ammonium ion selective electrode and its application in flow-injection analysis," Talanta XP004571139 ISSN: 0039-9140; vol. 64, No. 3 Oct. 20, 2004, 603-608 pgs.
Ratner, Buddy D. "Reducing capsular thickness and enhancing angiogenesis around implant drug release systems," Journal of Controlled Release 2002, 78, pp. 211-218.
"Response to Communication pursuant to Article 94 (3) EPC," for EP Patent Application No. 07762189.4 filed Jul. 27, 2009 (9 pages).
"Response to Communication pursuant to Article 94 (3) EPC," for EP Patent Application No. 07762189.4 filed Sep. 28, 2010 (10 pages).
Russell, Alan J. et al., "Biomaterials for Mediation of Chemical and Biological Warfare Agents," Annu. Rev. Biomed. Eng. 2003, 5, pp. 1-27.
Schaffar, Bernhard P. "Thick film biosensors for metabolites in undiluted whole blood and plasma samples," Anal Bioanal Chem 2002, 372, pp. 254-260.
Schneider, J. et al., "Hydrogel matrix for three enzyme entrapment in creatine/creatinine amperometric biosensing," Analytica Chimica Acta 1996, 325, pp. 161-167.
Sharma, Anjal C. et al., "A general photonic crystal sensing motif: Creatinine in bodily fluids," Journal of the American Chemical Society vol, 126, No. 9, Mar. 10, 2004 pp. 2971-2977 Mar. 10, 2004, 2971-2977 pgs.
Shin, Jae H. et al., "A Planar Amperometric Creatinine Biosensor Employing an Insoluble Oxidizing Agent for Removing Redox-Active Interferences," Anal. Chem. 2001, 73, pp. 5965-5971.
Shirreffs, S. M. et al., "The effect of posture change on blood volume, serum potassium and whole body electrical impedance," European Journal of Applied Physiology (1994) 69:461-463 (3 pages).
Singh, et al., "Serum potassium changes during controlled hyperventilation," J of Anaes Clin Phar, Jul. 1900; 6(3): 231-234.
Soldatkin, Alexey P. et al., "Creatinine sensitive biosensor based on ISFETs and creatinine deiminase immobilised in BSA membrane," Talanta XP002510643 ISSN: 1873-3573; vol. 58, No. 2 Aug. 23, 2002, 351-357 pgs.
Stadler, G. et al., "Changes in Plasmatic Electrolyte Levels during and after Intentional Hyperventilation," Praxis, (Bern 1994), Mar. 1995; vol. 84, No. 12, pp. 328-334 (7 pages).
Suk Han, In et al., "Constant-Volume Hydrogel Osmometer: A New Device Concept for Miniature Biosensors," Biomacromolecules 2002, 3, pp. 1271-1275.
Tanabe, Yasuhiko et al., "Exercise-Induced Rise in Arterial Potassium in Patients with Chronic Heart Failure," Chest (1999) vol. 116 No. 1, pp. 88-96 (9 pages).
Tohda, Koji et al., "A Microscopic, Continuous, Optical Monitor for Interstitial Electrolytes and Glucose," Chemphyschem 2003, pp. 155-160.
Tohda, Koji et al., "Micro-miniature Autonomous Optical Sensor Array for Monitoring Ions and Metabolites 1: Design, Fabrication, and Data Analysis," Analytical Sciences. vol. 22 Mar. 2006, pp. 383-388.
Trickey, Peter et al., "Monomeric sarcosine oxidase: structure of a covalently flavinylated amine oxidizing enzyme," Structure 1999, vol. 7, No. 3, pp. 331-345.
Tsai, Hc et al., "Simultaneous Determination of Renal Clinical Analytes in Serum using Hydrolase- and Oxidase-Encapsulated Optical Array Biosensors," Analytical Biochemistry 334 2004, pp. 183-192.
Tsuchida, Toshio et al., "Multi-Enzyme Membrane Electrodes for Determination of Creatinine and Creatine in Serum," Clin. Chem. 1983, 29/1, pp. 51-55.
Voskerician, Gabriela et al., "Biocompatibility and Biofouling of MEMs Drug Delivery Devices," Biomaterials 24 2003, pp. 1959-1967.
Wasserman, Karlman et al., "Mechanism of the exercise hyperkalemia: an alternate hypothesis," Journal of Applied Physiology (1997) vol. 83 No. 2, 631-643 (13 pages).
International Preliminary Report on Patentability for PCT Application No. PCT/US2016/038989 dated Jan. 11, 2018 (8 pages).
International Search Report and Written Opinion for PCT Application No. PCT/US2016/038989 dated Oct. 26, 2016 (12 pages).
Response to Communication Pursuant to Rules 161(1) and 162 EPC for European Patent Application No. 16741428.3 filed with the EPO Aug. 21, 2018 (17 pages).
First Office Action for Chinese Patent Application No. 201680037681.6 dated Dec. 25, 2019 (20 pages) with English Translation.
Office Action for Japanese Patent Application No. 2017566292 dated Feb. 25, 2020 (11 pages) with English Translation.

\* cited by examiner

SYSTEMS AND METHODS FOR NORMALIZATION OF CHEMICAL SENSOR DATA BASED ON FLUID STATE CHANGES

This application claims the benefit of U.S. Provisional Application No. 62/185,958, filed Jun. 29, 2015, the content of which is herein incorporated by reference in its entirety.

FIELD

Embodiments herein relate to implantable medical systems, devices and methods including chemical sensors.

BACKGROUND

The concentration of various physiological components can influence, and be influenced by, the functioning of various bodily organs. In addition, the concentration of various physiological components can also impact the measurement of organ function. By way of example, potassium is an important physiological electrolyte. Extracellular potassium concentration is normally maintained between 4.0 and 4.5 mEq/L through an interplay of potassium excretion and consumption. An excess of potassium is referred to as hyperkalemia. Hyperkalemia can induce cardiac arrhythmias. In addition, hyperkalemia can also lead to abnormal ST segments in cardiac electrogram data making it more difficult to properly diagnose myocardial ischemia.

SUMMARY

Embodiments herein include implantable medical systems, devices and method including chemical sensors. In an embodiment, an implantable medical device system is including having a chemical sensor; a fluid state sensor selected from the group consisting of a posture sensor; an activity sensor; and a respiration sensor. The implantable medical device system can further include normalization circuitry receiving data from the chemical sensor and the fluid state sensor and normalizing the chemical sensor data based on data from the fluid state sensor.

In addition, or alternatively, in various embodiments herein, the normalization circuitry can discard chemical sensor data, ignore chemical sensor data, or suspend chemical sensor data collection when the corresponding fluid state sensor data indicates a fluid state exceeding a threshold value.

In addition, or alternatively, in various embodiments herein the normalization circuitry can label data coming from the chemical sensor based on the corresponding data from the fluid state sensor.

In addition, or alternatively, in various embodiments herein the normalization circuitry can categorize chemical sensor data based on corresponding fluid state data. In addition, or alternatively, in various embodiments herein the normalization circuitry can adjust alert and/or therapy thresholds according to the category. In addition, or alternatively, in various embodiments herein the normalization circuitry can adjust the chemical sensor data according to the category.

In addition, or alternatively, in various embodiments herein the normalization circuitry can match fluid state sensor data with chemical sensor data that is offset in time from one another. In addition, or alternatively, in various embodiments herein the normalization circuitry can use fluid state sensor data from an earlier time to process chemical sensor data from a later time.

In addition, or alternatively, in various embodiments herein the normalization circuitry can match a measured fluid state as determined by the fluid state data to a template for that fluid state. In addition, or alternatively, in various embodiments herein the normalization circuitry can further adjust the chemical sensor values according to the template.

In addition, or alternatively, in various embodiments herein the normalization circuitry can calculate a weighted average for the chemical sensor data with the weight based on the fluid state sensor data.

In addition, or alternatively, in various embodiments herein the chemical sensor data can be native values for amounts of a measured physiological analyte and the normalization circuitry generating a normalized value by increasing the native value when the fluid state sensor measured value indicates that the measured analyte has been decreased and decreasing the native value when the fluid state sensor measured value indicates that the measured analyte has been increased.

In addition, or alternatively, in various embodiments herein the implantable medical device system can further include therapy control circuitry controlling the parameters of therapy delivery to a patient. The therapy control circuitry can omit changes in physiological analyte concentrations from consideration when the normalization circuitry indicates that current chemical sensor data is unreliable.

In addition, or alternatively, in various embodiments herein the implantable medical device system can further include recorder circuitry to record the data produced by the chemical sensor and/or the fluid state sensor and time stamps regarding the same.

In addition, or alternatively, in various embodiments herein the normalization circuitry can produce normalized chemical sensor data and the system can include recording circuitry to record the normalized chemical sensor data and time stamps regarding the same.

In addition, or alternatively, in various embodiments herein the implantable medical device system can further include telemetry circuitry for sending information regarding the chemical sensor data and fluid state sensor data wirelessly outside the body of a patient into which the system is implanted.

In addition, or alternatively, in various embodiments herein the chemical sensor can be a sensor selected from the group consisting of optical, electrochemical, electrical, mass sensitive, magnetic, and thermometric sensors. In addition, or alternatively, in various embodiments herein the chemical sensor can generate native values for analytes selected from the group consisting of electrolytes, hormones, proteins, peptides, sugars, and metabolites.

In addition, or alternatively, in various embodiments herein the chemical sensor and the fluid state sensor are part of a single integrated device. Alternatively, in various embodiments herein the chemical sensor and the fluid state sensor are part of separate devices.

In various embodiments, an implantable medical device system is included herein. The system can include a chemical sensor and a fluid state sensor. The fluid state sensor can be selected from the group consisting of a posture sensor, an activity sensor, and a respiration sensor. The processor can be configured to receive data from the chemical sensor and the fluid state sensor. The processor can also be configured to normalize the chemical sensor data based on data from the fluid state sensor.

In an embodiment, a method of operating an implantable medical device system is included. The method can include measuring the amount of a chemical analyte using a chemical sensor, measuring the fluid status in a patient using a fluid state sensor, and normalizing the measured amount of the chemical analyte as indicated by the chemical sensor using normalization circuitry based on data from the fluid state sensor.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
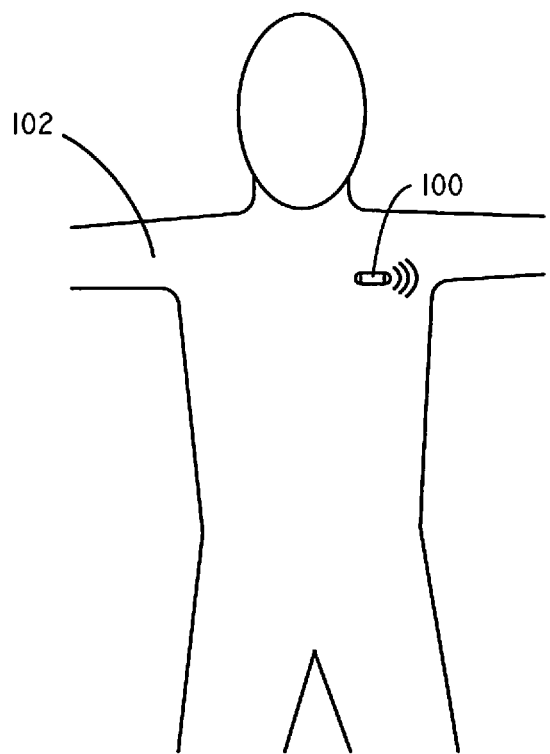
FIG. 1 is a schematic view of an implantable medical system in accordance with various embodiments herein.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the scope to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

There are many challenges associated with the use of implanted chemical sensors. For example, some implantable chemical sensors have suffered from problems including substantial signal drift over time making chronic use in the in vivo environment difficult. In addition, implanted chemical sensors have been observed to provide inconsistent data with the measured concentrations at one time varying substantially from the measured concentrations at a later time, in some cases only tens of minutes later.

Applicants have discovered that the consistency of data provided by chemical sensors can be increased by accounting for the fluid state of the patient and changes thereto. By way of example, it has been found that state changes associated with activity, posture, and respiration can result in local and/or transitory changes in the concentrations of physiological analytes in the areas in which sensors may be implanted. For example, recumbency (lying down) causes interstitial fluid movement to the vascular system having the effect of diluting the blood. Recumbency for approximately 3 hours can result in a 15% greater plasma volume. As another example, plasma potassium concentrations increase during activity such as exercise and cessation of exercise results in a rapid decrease in plasma potassium. Also, increased respiration can lead to a higher pH value for bodily fluids such as plasma and lower measured potassium levels.

For purposes herein, changes in activity, posture and respiration can be considered as fluid state changes because of their impact on fluid state as described above. In accordance with embodiments herein, which can include measuring the state changes themselves, it is possible to normalize or correct the data provided by the chemical sensors leading to more reliable physiological analyte data. As such, the effect of activity, posture and respiration on chemical sensor data can be mitigated or otherwise accounted for. In addition to activity, posture and respiration, changed in fluid state might be caused by, for example, a change in hydration status, a medication, diet, trauma, a medical condition, heart rate, cardiac output and/or an emotional state.

In some aspects, normalization of data can include correcting the native or raw data provided by a chemical sensor to account for fluid state changes in order to produce corrected or normalized data. In some embodiments, correcting the native or raw data can be performed in a proportional manner the changes indicated by the fluid state sensor data. Such proportionality can include linear, exponential, or logarithmic proportionality. In some embodiments, correcting the native or raw data can be performed by calculating a weighted average value for a timer period wherein the chemical sensor data corresponding to times when fluid state is at a normal level are weighted more heavily than the chemical sensor data corresponding to times when fluid state deviates from a normal level. In some embodiments, correcting the native or raw data can be performed by applying a function that is derived through analysis of a training data set generated by observing the relationship between fluid state change and chemical sensor data change by having the patient, or a class of patients, assume various activity levels, postures, and/or respiration levels and observing the resulting chemical sensor values. In some embodiments, correcting the native or raw data can be performed by matching the native or raw data to corresponding template providing specific procedures for the correction and then following such procedures. In some aspects, normalization of data can include discarding or otherwise not acting upon native or raw data provided by a chemical sensor. Further aspects of exemplary normalization procedures are described in greater detail below.

Referring now to FIG. 1, a schematic view is shown of an implantable medical device 100 consistent with various embodiments herein. In some embodiments, the implantable medical device 100 can include an implantable loop recorder, implantable monitor device, or the like. The implantable medical device 100 can be implanted within the body of a patient 102. Various implant sites can be used including areas on the limbs, the upper torso, the abdominal area, and the like.

Figure 2:
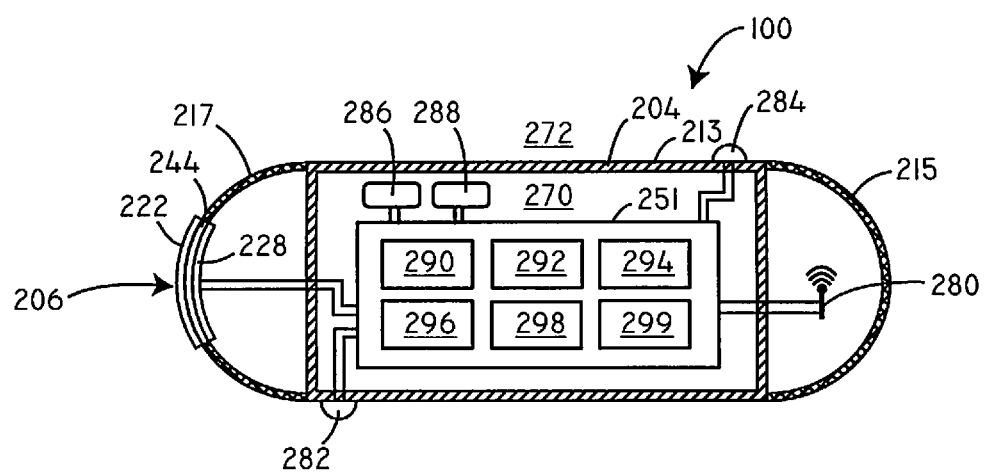
FIG. 2 is a schematic cross-sectional view of an implantable medical device in accordance with various embodiments herein.

Referring now to FIG. 2, a schematic cross-sectional view of the implantable medical device 100 is shown in accordance with various embodiments herein. The implantable medical device 100 includes a housing 204. The housing 204 of the implantable medical device 100 can include various materials such as metals, polymers, ceramics, and the like. In some embodiments, the housing 204 can be a single integrated unit. In other embodiments, the housing 204 can include a main segment 213 along with appendage segments 215 and 217. In one embodiment, the housing 204, or one or more portions thereof, is formed of titanium. In some embodiments, one or more segments of the housing 204 can be hermetically sealed. In some embodiments, the main segment 213 is formed of a metal and the appendage segments 215 and 217 are formed from a polymeric material.

The housing 204 defines an interior volume 270 that in some embodiments is hermetically sealed off from the area 272 outside of the device 100. The device 100 can include circuitry 251. The circuitry can include various components, such as components 290, 292, 294, 296, 298, and 299. In some embodiments, these components can be integrated and in other embodiments these components can be separate. In some embodiments, the components can include one or more of a microprocessor, memory circuitry (such as random access memory (RAM) and/or read only memory (ROM)), recorder circuitry, telemetry circuitry, sensor interface circuitry, power supply circuitry (which can include one or more batteries), normalization circuitry, control circuitry, and the like. In some embodiments recorder circuitry can record the data produced by the chemical sensor and/or the fluid state sensor and record time stamps regarding the same. In some embodiments, the circuitry can be hardwired to execute various functions while in other embodiments, the circuitry can be implemented as instructions executing on a microprocessor or other computation device.

The implantable medical device 100 can include, for example, an electrical field sensor that is configured to generate a signal corresponding to cardiac electric fields. The electrical field sensor can include a first electrode 282 and a second electrode 284. In some embodiments, the housing 204 itself can serve as an electrode. The electrodes can be in communication with the electrical field sensor. The electrical field sensor can include a circuit in order to measure the electrical potential difference (voltage) between the first electrode 282 and the second electrode 284. The implantable medical device 100 can also include an antenna 280, to allow for unidirectional or bidirectional wireless data communication.

The implantable medical device 100 can also include a chemical sensor 206. In the embodiment shown in FIG. 2, the chemical sensor is an optical chemical sensor. However, in other embodiments the chemical sensor can be a potentiometric chemical sensor. The chemical sensor 206 can specifically include a chemical sensing element 222, an optical window 244, and an electro-optical module 228. The electro-optical module 228 can be in electrical communication with the circuitry 251 within the interior volume 270, and in some embodiments, the control circuitry 251 is configured to selectively activate the chemical sensor 206. The chemical sensor 206 can be configured to be chronically implanted.

The chemical sensor 206 can include an electro-optical module 228 coupled to the optical window 244. The electro-optical module 228 can specifically include one or more optical excitation assemblies. Each optical excitation assembly can include various light sources such as light-emitting diodes (LEDs), vertical-cavity surface-emitting lasers (VC-SELs), electroluminescent (EL) devices or the like. The electro-optical module 228 can also include one or more optical detection assemblies. Each optical detection assembly can include one or more photodiodes, avalanche photodiodes, a photodiode array, a photo transistor, a multi-element photo sensor, a complementary metal oxide semiconductor (CMOS) photo sensor, or the like.

The chemical sensing element 222 can be disposed on the optical window 244. The chemical sensing element 222 can be configured to detect a physiological analyte by exhibiting an optically detectable response to the physiological analyte. Specific examples of physiological analytes are discussed in greater detail below. In operation, analytes of interest from the in vivo environment can diffuse into the chemical sensing element 222 causing a detectable change in the optical properties of the chemical sensing element 222. Light can be generated by the electro-optical module 228 and can pass through the optical window 244 and into the chemical sensing element 222. Light can then either be preferentially reflected from or re-emitted by the chemical sensing element 222 proportional to the sensed analyte and pass back through the optical window 244 before being received by the electro-optical module 228. Various aspects of exemplary chemical sensors are described in greater detail in U.S. Pat. No. 7,809,441, the content of which is herein incorporated by reference in its entirety.

In some embodiments the chemical sensing element 222 is located in a fluid such as blood, interstitial fluid, urine, lymph or chyle and senses analytes in a fluid. In other embodiments, the chemical sensing element 222 is located in a solid tissue such as muscle, fat, bone, bone marrow, organ tissues (e.g. kidney, liver, brain, lung, etc.) and senses analytes in a solid tissue.

Figure 3:
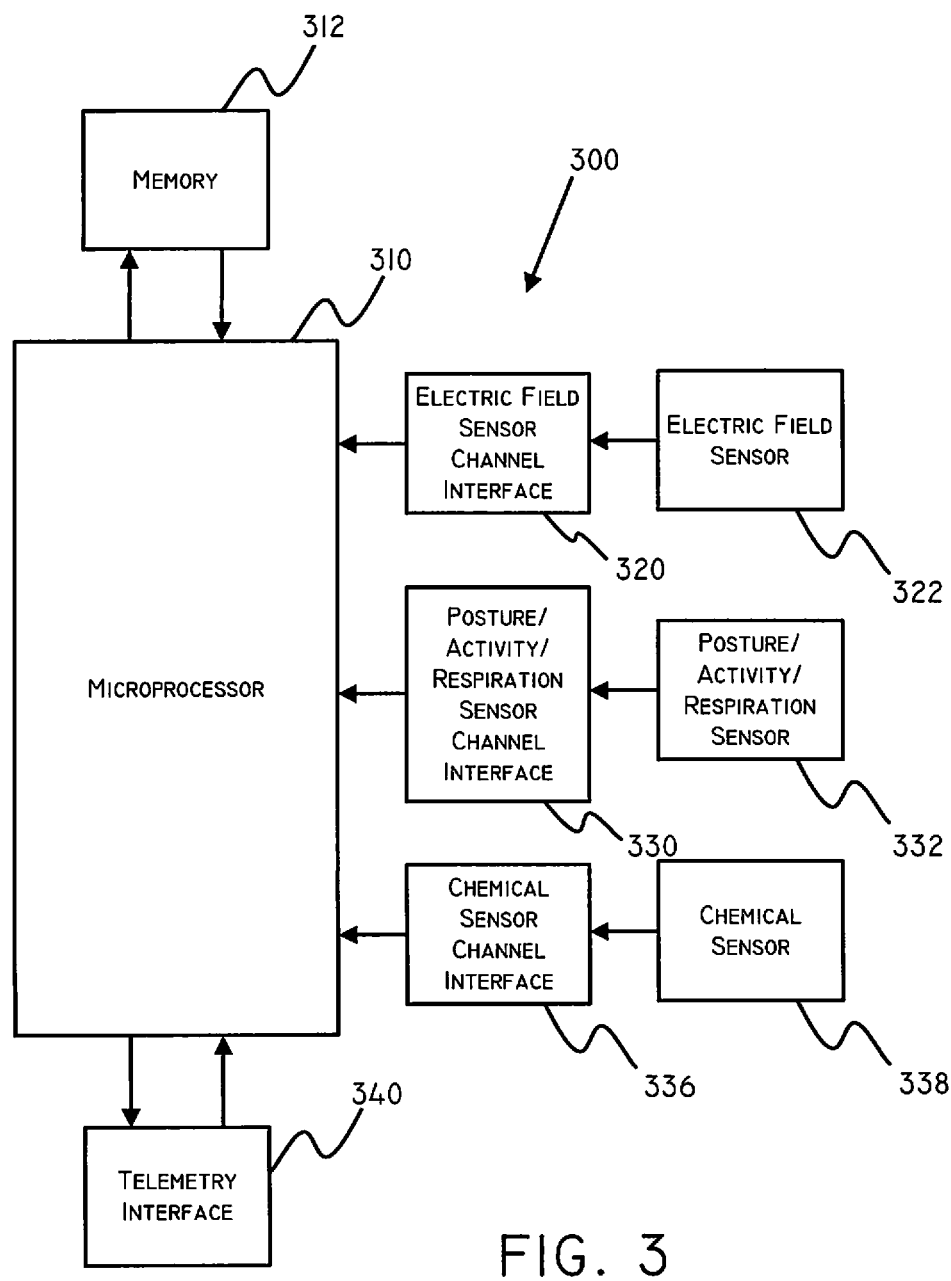
FIG. 3 is a schematic diagram of components of an implantable medical device in accordance with various embodiments herein.

Elements of various embodiments of an implantable medical device are shown in FIG. 3. However, it will be appreciated that some embodiments can include additional elements beyond those shown in FIG. 3. In addition, some embodiments may lack some elements shown in FIG. 3. The medical device 300 can gather information through one or more sensing channels. A microprocessor 310 can communicate with a memory 312 via a bidirectional data bus. The memory 312 can include read only memory (ROM) or random access memory (RAM) for program storage and RAM for data storage.

The implantable medical device can include one or more electrodes 322 and an electric field sensor channel interface 320 which can communicate with a port of microprocessor 310. The implantable medical device can also include one or more posture, activity, or respiration sensors 332 and a posture/activity/respiration sensor channel interface 330 which can communicate with a port of microprocessor 310. The implantable medical device can also include a chemical sensor 338 and a chemical sensor channel interface 336 which can communicate with a port of microprocessor 310. The channel interfaces 320, 330 and 336 can include various components such as analog-to-digital converters for digitizing signal inputs, sensing amplifiers, registers which can be written to by the control circuitry in order to adjust the gain and threshold values for the sensing amplifiers, and the like. A telemetry interface 340 is also provided for communicating with external devices such as a programmer, a home-based unit and/or a mobile unit (e.g a cellular phone).

Figure 4:
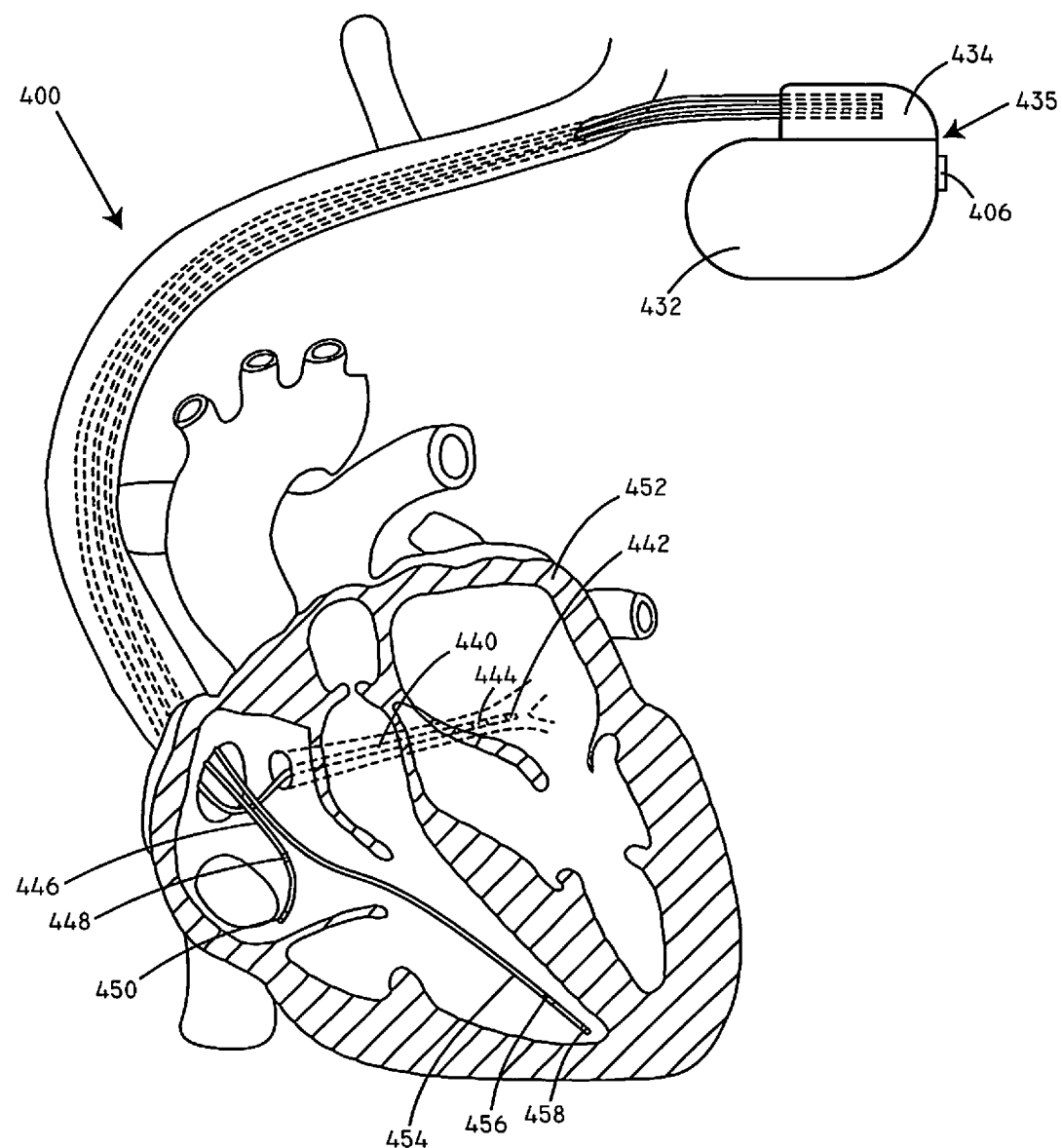
FIG. 4 is a schematic view of an implantable medical system in accordance with various embodiments herein.

Although the posture, activity, or respiration sensors 332 are shown as part of medical device 300 in FIG. 3 it is realized that in some embodiments one or more of the posture, activity, or respiration sensors could be separate from medical device 300. In various embodiments one or more of the posture, activity, or respiration sensors are within another implanted medical device communicatively coupled to medical device 300 via telemetry interface 340. In various embodiments one or more of the posture, activity, or respiration sensors are external to the body and are coupled to medical device 300 via telemetry interface 340. Referring now to FIG. 4, a schematic view is shown of an implantable medical system 400. The implantable medical system 400 includes an implantable medical device 435 and one or more stimulation leads 440, 446, and 454. In various embodiments, the implantable medical device 435 can include a cardiac rhythm management device, such as a pacemaker, a cardiac resynchronization therapy (CRT) device, a remodeling control therapy (RCT) device, a cardioverter/defibrillator, or a device providing two or more of these therapies. In some embodiments, the implantable medical device 435 can be, or include, a neurological stimulation device.

The implantable medical device 435 can include a pulse generator housing 432 and a header 434. The term "pulse generator housing" as used herein shall refer to the part or parts of an implanted medical device, such as a cardiac rhythm management device or a neurological therapy device, containing the power source and circuitry for delivering pacing therapy, electrical stimulation, and/or shock therapy. Together, the pulse generator housing 432, the contents therein, and the header 434 can be referred to as a pulse generator. It will be appreciated that embodiments herein can also be used in conjunction with implantable medical devices that may lack pulse generators such as monitoring devices and drug delivery devices.

In FIG. 4, the proximal ends of the stimulation leads 440, 446, and 454 are disposed within the header 434. The stimulation leads 440, 446, and 454 can pass to the heart 452 transvenously. In this view, stimulation lead 440 passes into the coronary venous system, stimulation lead 446 passes into the right atrium, and stimulation lead 454 passes into the right ventricle. However, it will be appreciated that stimulation leads can be disposed in various places within or around the heart. Stimulation lead 440 includes a tip electrode 442 and a ring electrode 444. Stimulation leads 446 and 454 also include tip electrodes 450 and 458 and ring electrodes 448 and 456, respectively. It will be appreciated that stimulation leads can include different numbers of electrodes. For example, in some embodiments, a stimulation lead may only include a single electrode and in some embodiments a stimulation lead may include more than two electrodes. Depending on the configuration, the stimulation leads can provide electrical and/or optical communication between the distal ends of the stimulation leads and the pulse generator. In operation, the pulse generator may generate pacing pulses or therapeutic shocks which are delivered to the heart 452 via the electrodes of the stimulation leads. In many embodiments, the stimulation leads include a material that is electrically conductive in order to deliver the pacing pulses or therapeutic shocks.

Figure 5:
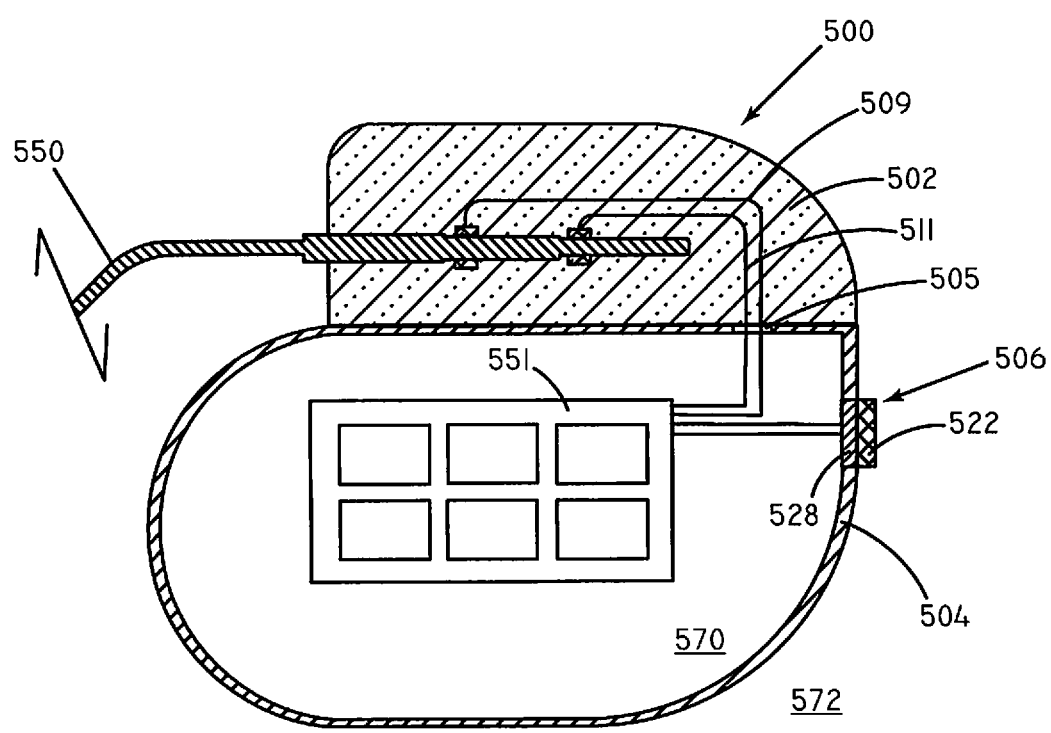
FIG. 5 is a schematic cross-sectional view of an implantable medical device in accordance with various embodiments herein.

The implantable medical system 400 can also be configured to sense electrical activity of the heart. By way of example, the implantable medical system 400 can include an electrical field sensor (such as shown in FIG. 5 as part of control circuitry 551). Specifically, the implantable medical system 400 can use one or more electrodes, such as the electrodes on the stimulation leads 442, 444, 448, 450, 456, and/or 458, in order to sense electrical activity of the heart, such as a time-varying electrical potential. In some embodiments, the pulse generator housing 432 can serve as an electrode for purposes of sensing electrical activity and/or delivering electrical stimulation.

The implantable medical system 400 can also include a chemical sensor 406. The chemical sensor 406 can be configured to measure the concentration of physiological analytes such as those described below.

Referring now to FIG. 5, a schematic cross-sectional view of an implantable medical device 500 is shown in accordance with various embodiments herein. The implantable medical device 500 includes a header assembly 502 and a housing 504. The housing 504 of the implantable medical device 500 can include various materials such as metals, polymers, ceramics, and the like. In one embodiment, the housing 504 is formed of titanium. The header assembly 502 can be coupled to one or more electrical stimulation leads 550. The header assembly 502 serves to provide fixation of the proximal end of one or more leads and electrically couples the leads to components within the housing 504. The header assembly 502 can be formed of various materials including metals, polymers, ceramics, and the like.

The housing 504 defines an interior volume 570 that is hermetically sealed off from the volume 572 outside of the device 500. Various electrical conductors 509, 511 can pass from the header 502 through a feed-through structure 505, and into the interior volume 570. As such, the conductors 509, 511 can serve to provide electrical communication between the electrical stimulation lead 550 and control circuitry 551 disposed within the interior volume 570 of the housing 504. The control circuitry 551 can include various components such as a microprocessor, memory (such as random access memory (RAM) and/or read only memory (ROM)), a telemetry module, electrical field sensor and stimulation circuitry, a power supply (such as a battery), and an optical sensor interface channel, amongst others.

The implantable medical device 500 can incorporate, for example, an electrical field sensor that is configured to generate a signal corresponding to cardiac electric fields. The electrical field sensor can include a first electrode and a second electrode. The electrodes of the electrical field sensor can be the same electrodes used to provide electrical stimulation (such as referred to with respect to FIG. 4) or can be different electrodes. In some embodiments, one or more electrodes can be mounted on one or more electrical stimulation leads 550. In some embodiments, the housing 504 can serve as an electrode. The electrodes can be in communication with the electrical field sensor and stimulation circuitry. The electrical field sensor can include a circuit (such as within control circuitry 551) in order to measure the electrical potential difference (voltage) between the first electrode and the second electrode.

The implantable medical device 500 can also include a chemical sensor 506. In the embodiment shown in FIG. 5, the chemical sensor is a potentiometric chemical sensor. The chemical sensor 506 can specifically include a receptor module 522, and a transducer module 528. The transducer module 528 can be in electrical communication with the circuitry 551 within the interior volume 570, and in some embodiments, the control circuitry 551 is configured to selectively activate the chemical sensor. The chemical sensor 506 can be configured to be chronically implanted.

The chemical sensor 506 can be configured to detect a physiological analyte by exhibiting an electrical signal response to the physiological analyte. In operation, analytes of interest from the in vivo environment can contact the receptor module 522 causing a detectable change in the electrical properties of the same. The transducer module 528 can then be used to process and/or propagate the signal created by the receptor module 522.

Figure 6:
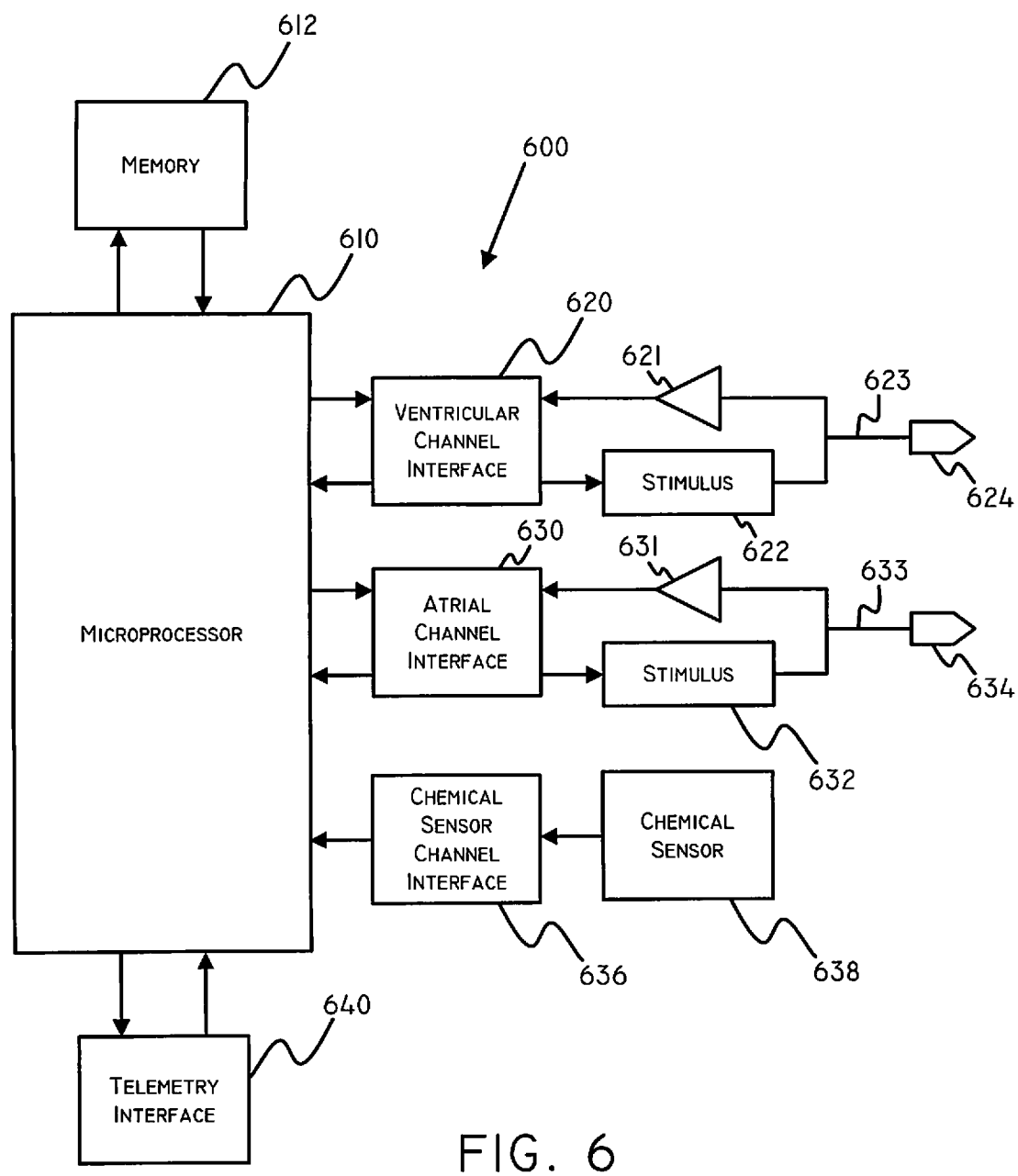
FIG. 6 is a schematic diagram of components of an implantable medical device in accordance with various embodiments herein.

Elements of some embodiments of an implantable medical device are shown in FIG. 6. However, it will be appreciated that some embodiments can include additional elements beyond those shown in FIG. 6. In addition, some embodiments may lack some elements shown in FIG. 6. The medical device 600 can sense cardiac events through one or more sensing channels and outputs pacing pulses to the heart via one or more pacing channels in accordance with a programmed pacing mode. A microprocessor 610 communicates with a memory 612 via a bidirectional data bus. The memory 612 typically comprises read only memory (ROM) or random access memory (RAM) for program storage and RAM for data storage.

The implantable medical device can include atrial sensing and pacing channels comprising at least a first electrode 634, lead 633, sensing amplifier 631, output circuit 632, and an atrial channel interface 630 which can communicate bidirectionally with a port of microprocessor 610. In this embodiment, the device also has ventricular sensing and pacing channels comprising at least a second electrode 624, lead 623, sensing amplifier 621, output circuit 622, and ventricular channel interface 620. For each channel, the same lead and electrode are used for both sensing and pacing. The channel interfaces 620 and 630 include analog-to-digital converters for digitizing sensing signal inputs from the sensing amplifiers and registers which can be written to by the control circuitry in order to output pacing pulses, change the pacing pulse amplitude, and adjust the gain and threshold values for the sensing amplifiers. The implantable medical device can also include a chemical sensor 638 and a chemical sensor channel interface 636. A telemetry interface 640 is also provided for communicating with an external programmer.

Figure 7:
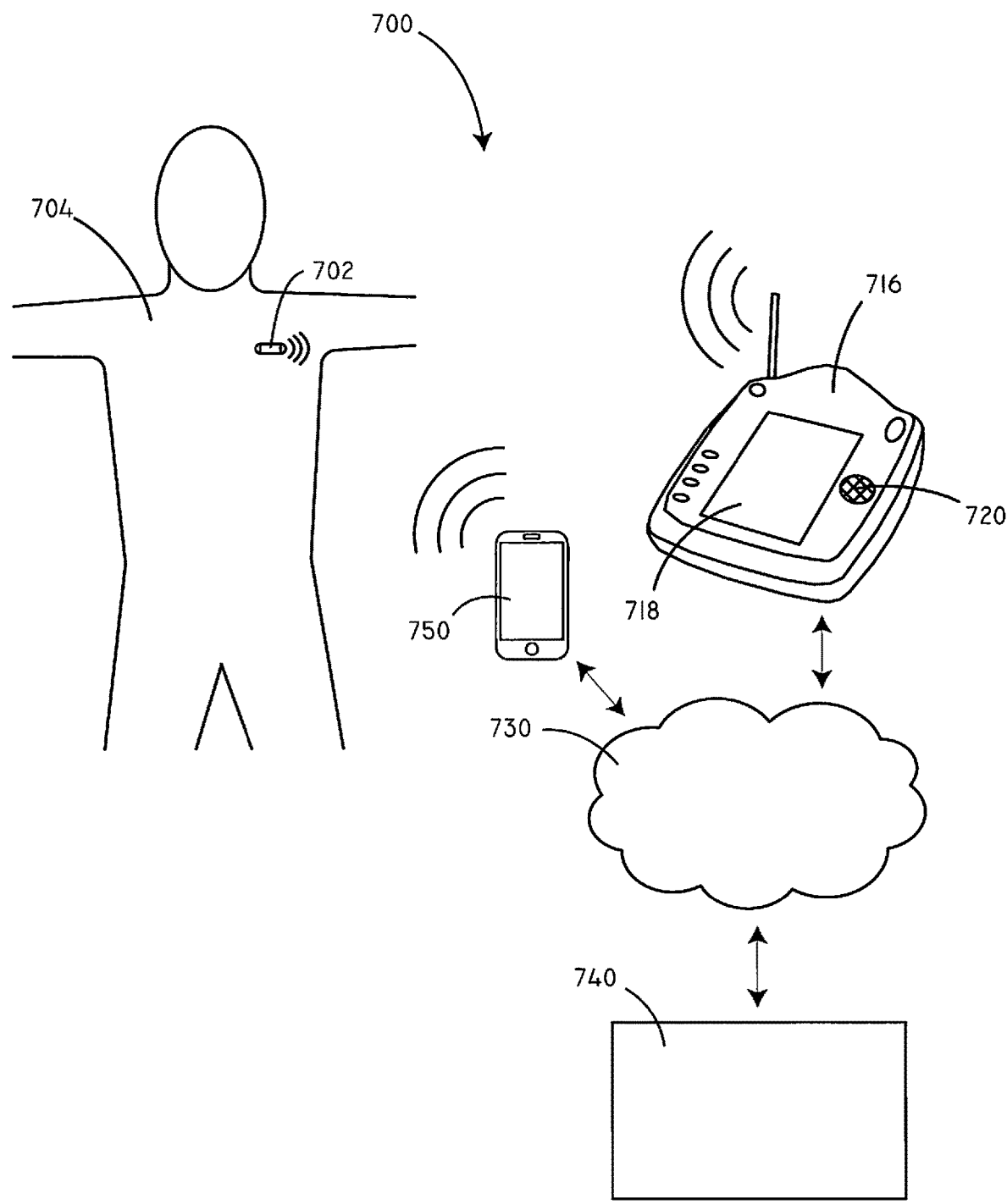
FIG. 7 is a schematic view of an implantable medical system in accordance with various embodiments herein.

Referring now to FIG. 7, a schematic view is shown of an implantable medical system 700 in accordance with various embodiments herein. In some embodiments, implantable medical system 700 can include an implantable medical device 702 such as an implantable loop recorder, implantable monitor device, a cardiac rhythm management device (such as a pacemaker, a cardiac resynchronization therapy (CRT) device, a remodeling control therapy (RCT) device, a cardioverter/defibrillator, or a pacemaker-cardioverter/defibrillator), a neurostimulator device, or the like. The implantable medical device 702 can be implanted within the body of a patient (or subject) 704. Various implant sites can be used including, but not limited to, areas on the limbs, the upper torso, the abdominal area, and the like. The system 700 can also include an external interface device 716. The external interface device 716 can include a video output 718 and/or an audio output 720. The external interface device 716 can communicate with the implantable device 702 wirelessly. The external interface device 716 can take on many different forms. In some embodiments, the external interface device 716 can include a programmer or programmer/recorder/monitor device. In some embodiments, the external interface device 716 can include a patient management system. An exemplary patient management system is the LATITUDE® patient management system, commercially available from Boston Scientific Corporation, Natick, Mass. Aspects of an exemplary patient management system are described in U.S. Pat. No. 6,978,182, the contents of which are herein incorporated by reference. In some embodiments, the external interface device 716 can include a hand-held monitoring device.

In some embodiments, the external interface device 716 can send and/or receive data through a data network 730 such as the Internet or a private data network. Through the data network 730, the external interface device 716 can send to and/or receive data from a remote patient management system 740 which can include one or servers (physical or virtual), databases, and user interfaces.

In some embodiments implantable medical device 702 can send or receive data directly to or from handheld device 750. In other embodiments handheld device 750 receives or sends data from or to implantable medical device 702 via external interface device 716 and data network 730. Handheld device 750 may be, for example, a smartphone, cellular phone or a device specifically made to interface with handheld device 750.

Patient management system 740 or handheld device 750 may be used by a patient, a healthcare professional or a caregiver such as a family member. In an embodiment patient management system 740 or handheld device 750 may be used in a mode wherein only display of information from implantable medical device 702 is available. In another embodiment patient management system 740 or handheld device 750 may be used in a mode wherein both display of data from, and programming of parameters within, implantable medical device 702 are available. In an embodiment, handheld device 750 may be used to trigger data storage within implantable medical device 702. In an embodiment the functionality of patient management system 740 or handheld device 750 is configured for a healthcare professional wherein, for example, healthcare functionality provides broad access to data and programming. In another embodiment the functionality of patient management system 740 or handheld device 750 are configured for a patient wherein, for example, healthcare patient functionality provides limited access to data and programming.

Chemical Sensors

Chemical sensors herein can be of various types. In some embodiments, the physiological concentration of an analyte is sensed directly. In other embodiments, the physiological concentration of an analyte is sensed indirectly. By way of example, a metabolite of a particular analyte can be sensed instead of the particular analyte itself. In other embodiments, an analyte can be chemically converted into another form in order to make the process of detection easier. By way of example, an enzyme can be used to convert an analyte into another compound that is easier to detect. For example, the hydrolysis of creatinine into ammonia and N-methylhydantoin can be catalyzed by creatinine deiminase and the resulting ammonia can be detected by a chemical sensor.

In some embodiments, chemical sensors herein can include at least two functional elements: a receptor and a transducer. It will be appreciated that other elements can also be included. The receptor part of a chemical sensor can transform chemical information into a form of energy or signal that can be measured by the transducer. The transducer can transform and/or convey the energy or signal carrying the chemical information so as to provide a useful analytical signal.

Chemical sensors can include optical devices that utilize changes of optical phenomena or properties, which are the result of an interaction of the analyte with the receptor part of the sensor. Such optical properties can include: absorbance, caused by the absorptivity of the analyte itself or by a reaction with some suitable indicator; reflectance, using a bodily component, tissue, or fluid, or using an immobilized indicator; luminescence, based on the measurement of the intensity of light emitted by a chemical reaction in the receptor system; fluorescence, measured as the positive emission effect caused by irradiation or selective quenching of fluorescence; refractive index, measured as the result of a change in solution composition, in some cases including surface plasmon resonance effects; optothermal effects, based on a measurement of the thermal effect caused by light absorption; light scattering; or the like. In some embodiments, optical chemical sensors can include an optode.

Chemical sensors can also include electrochemical devices that transform the effect of the electrochemical interaction between an analyte and an electrode into a useful signal. Such sensors can include voltammetric sensors, including amperometric devices. Also included are sensors based on chemically inert electrodes, chemically active electrodes and modified electrodes. Also included are sensors with and without (galvanic sensors) a current source. Sensors can also include potentiometric sensors, in which the potential of the indicator electrode (ion-selective electrode, redox electrode, metal oxide electrode, or the like) is measured against a reference electrode. Sensors can include chemically sensitized field effect transistors (CHEMFET) in which the effect of the interaction between the analyte and the active coating is transformed into a change of the source-drain current. Sensors can include potentiometric solid electrolyte gas sensors.

Chemical sensors can also include electrical devices based on measurements, where no electrochemical processes take place, but the signal arises from the change of electrical properties caused by interaction with the analyte. Such sensors can include metal oxide semiconductor sensors based on reversible redox processes of analyte gas components, organic semiconductor sensors, based on the formation of charge transfer complexes, which modify the charge carrier density, electrolytic conductivity sensors, and electric permittivity sensors.

Chemical sensors can also include mass sensitive devices that transform the mass change at a specially modified surface into a change of a property of the support material. The mass change can be caused by accumulation of the analyte. Such sensors can include piezoelectric devices based on the measurement the frequency change of the quartz oscillator plate caused by adsorption of a mass of the analyte at the oscillator and surface acoustic wave devices that depend on the modification of the propagation velocity of a generated acoustical wave affected by the deposition of a definite mass of the analyte.

Chemical sensors can also include magnetic devices based on the change of paramagnetic properties of a gas being analyzed. Chemical sensors can also include thermometric devices based on the measurement of the heat effects of a specific chemical reaction or adsorption that involves the analyte.

In one example of the operation of an optical chemical sensor, analytes of interest from the in vivo environment can diffuse into a chemical sensing element causing a detectable change in the optical properties of the chemical sensing element. Light can be generated by an optical excitation device or emitter, such as an LED or similar device, and can pass through the optical window and into the chemical sensing element. Light can then either be preferentially reflected from or re-emitted by the chemical sensing element proportionally to the sensed analyte and pass back through the optical window before being received by a light detection device or receiver, such as a charge-coupled device (CCD), a photodiode, a junction field effect transistor (JFET) type optical sensor, of complementary metal-oxide semiconductor (CMOS) type optical sensor. Various aspects of exemplary chemical sensors are described in greater detail in U.S. Pat. No. 7,809,441, the content of which is herein incorporated by reference in its entirety. In another example of the operation of an optical chemical sensor, the optical properties of a tissue or fluid in the body can be directly analyzed. By way of example, light can be generated by an optical excitation device that can be delivered to a component, tissue, or fluid in the body and a light detection device can be used to sense an optical property of the light that has interfaced with the component, tissue, or fluid.

Fluid State Sensors

Fluid state sensors can include, but are not limited to, posture sensors, activity sensors, and respiration sensors. Fluid state sensors can include direct sensors wherein the sensed or measured aspect is directly sensed or measured. Fluid state sensors can also include indirect sensors, wherein the sensed or measured aspect is indirectly sensed or measured.

Posture, activity, and/or respiration can be sensed through various types of sensors such as acoustic sensors, ECG sensors, vibration sensors, hemodynamic sensors, impedance sensors, accelerometers, and the like. In some embodiments a particular type of sensor can be used to sense one or more of posture, activity, and respiration.

Examples of posture sensors can include implantable sensors that can be configured to detect, determine, or differentiate between patient postures. For example, the posture sensor can include an accelerometer, such as a 3-axis or 6-axis accelerometer, configured to provide information about whether the sensor implanted in the subject is vertically or horizontally oriented. In some embodiments, the posture sensor includes an impedance sensor to measure a trans-thoracic, vessel, or other impedance value known to vary with posture from which the posture of the patient can be determined. The impedance sensor can include at least two electrodes disposed in the patient's body and configured to detect electrical signals therein. In some embodiments, the posture sensor can include a pressure sensor to measure an internal pressure value. In various embodiments, such posture sensors can be calibrated by having the patient assume different postures and then recording the sensor data associated with those postures. Postures can then be later determined by comparing current sensor reading with previously recorded sensor readings matching different postures. It will be appreciated, however, that there are many ways of determining posture from such sensor data.

In some embodiments, the rate of posture change can also be determined by posture sensors. In general, the rate of posture change can be determined by combining time data in addition to positional data. Posture sensors that can provide data regarding the rate of posture change can include, for example, a 3-axis or 6-axis accelerometer configured to provide information about the rate of posture change by including time data along with positional data, amongst other approaches. Posture sensors that can provide data regarding the rate of posture change can also include one or more solid state gyroscopes configured to determine the rate of posture change.

Examples of activity sensors can include implantable sensors that can be configured to detect, determine, or differentiate between different levels of patient activity. For example, in some embodiments, the activity sensor can include a vibration sensor. In some embodiments, the vibration sensor can be an implantable accelerometer. The vibration sensor can be configured to receive vibrational energy from a patient and can be used to identify a level of activity for the patient such as the patient's physical activity level, such as a relative exercise or exertion level. In some embodiments, the activity sensor can be an impedance sensor configured to determine activity levels. The impedance sensor can include at least two electrodes disposed in the patient's body and configured to detect electrical signals therein. The device can be configured to receive electrical signal information from the impedance sensor to identify a detected or measured impedance between the two or more electrodes. In an example, a processor circuit can be used to process the received impedance information to identify cardiac activity, respiratory activity, muscle activity, vessel dimensional changes (e.g., using impedance plethysmography techniques), or other information about a patient's activity status. In some embodiments, the activity sensor can include an ECG sensor. The ECG sensor can include at least two electrodes disposed in the patient's body configured to detect electrical activity from the patient's body. The processor circuit can use the electrogram information to identify morphological characteristics (e.g., timings, amplitudes, shapes, etc.) that are indicative of patient activity.

Examples of respiration sensors can include implantable sensors that can be configured to detect, determine, or differentiate between different levels of patient respiration. The respiration sensor can be an implantable sensor configured to monitor subject chest expansion and contraction. In an example, the respiration sensor can be configured to provide information about a subject's tidal volume or minute ventilation. In some embodiments, the respiration sensor can be an acoustic sensor. The acoustic sensor can be an implantable transducer such as a microphone or accelerometer. The acoustic sensor can be configured to receive acoustic vibrational energy from a subject, such as in the audible spectrum. In an example, a portion of the circuitry can be configured to receive information from the acoustic sensor and identify respiration information. In some embodiments, the respiration sensor can be a vibration sensor. The vibration sensor can be an implantable transducer, such as an accelerometer. The vibration sensor can be configured to receive vibrational energy from a patient and can be used to identify respiration information. In some embodiments, the respiration sensor can be an impedance sensor configured to determine respiration data. The impedance sensor can include at least two electrodes disposed in the patient's body and configured to detect electrical signals therein. The device can be configured to receive electrical signal information from the impedance sensor to identify a detected or measured impedance between the two or more electrodes. In an example, a processor circuit can be used to process the received impedance information to identify respiration data.

Physiological Analytes

Examples of physiological analytes that can be measured in accordance with chemical sensors of embodiments herein can include, but are not limited to, electrolytes, hormones, proteins, sugars, metabolites, and the like.

Chemical sensors herein can be directed at a specific analyte or a plurality of different analytes. In an embodiment, the analyte sensed is one or more analytes relevant to cardiac health. In an embodiment, the analyte sensed is one or more analytes indicative of renal health. The analyte sensed can be an ion or a non-ion. The analyte sensed can be a cation or an anion. Specific examples of analytes that can be sensed include acetic acid (acetate), aconitic acid (aconitate), ammonium, blood urea nitrogen (BUN), B-type natriuretic peptide (BNP), bromate, calcium, carbon dioxide, cardiac specific troponin, chloride, choline, citric acid (citrate), cortisol, copper, creatinine, creatinine kinase, fluoride, formic acid (formate), glucose, hydronium ion, isocitrate, lactic acid (lactate), lithium, magnesium, maleic acid (maleate), malonic acid (malonate), myoglobin, nitrate, nitric-oxide, oxalic acid (oxalate), oxygen, phosphate, phthalate, potassium, pyruvic acid (pyruvate), selenite, sodium, sulfate, urea, uric acid, and zinc. Inorganic cations sensed by this method include but not limited to hydronium ion, lithium ion, sodium ion, potassium ion, magnesium ion, calcium ion, silver ion, zinc ion, mercury ion, lead ion and ammonium ion. Inorganic anions sensed by this method include but not limited to carbonate anion, nitrate anion, sulfite anion, chloride anion and iodide anion. Organic cations sensed by this method include but are not limited to norephedrine, ephedrine, amphetamine, procaine, prilocaine, lidocaine, bupivacaine, lignocaine, creatinine and protamine. Organic anions sensed by this method include but not limited to salicylate, phthalate, maleate, and heparin. Neutral analytes sensed by this method include but not limited to ammonia, ethanol, and organic amines. In an embodiment, ions that can be sensed include potassium, sodium, chloride, calcium, and hydronium (pH). In a particular embodiment, concentrations of both sodium and potassium are measured. In another embodiment, concentrations of both magnesium and potassium are measured.

In some embodiments, the analytes can specifically include one or more of sodium ion, magnesium ion, chloride ion, calcium ion, carbonate ion, phosphate ion, sulfate ion, insulin, aldosterone, troponin, glucose, creatinine, and BNP.

In some embodiments, the analytes can specifically include one or more of partial pressure of oxygen ($PaO_2$), partial pressure of carbon dioxide ($PaCO_2$) and oxygen saturation ($O_2Sat$).

Normalization

Various embodiments herein include normalization circuitry and/or execute an operation of normalization. It will be appreciated that normalization can include various steps. As such, normalization circuitry or modules herein can execute a number of specific steps.

In some embodiments, normalization can include modifying the value of chemical sensor data in order to mitigate the effects of varied fluid states, such as transitory fluid state changes, and create corrected or normalized chemical sensor data that more reliably reflects the actual physiological state of the patient or subject. By way of example, the normalization circuitry or module can take native (or raw) data as provided by the chemical sensor and then modify the same by doing at least one of increasing, decreasing, or maintaining the values thereof in order to result in normalized (or corrected) data.

In some embodiments, correcting the native or raw data can be performed in a manner that is proportional to the changes indicated by the fluid state sensor data. Such proportionality can include linear, exponential, or logarithmic proportionality. A baseline value for the fluid state sensors can be set or can be derived from evaluation of the fluid state sensor data over time. Then, to normalize pieces of the chemical sensor data, the corresponding chemical sensor data can be compared to the baseline values and the difference can be used to determine what changes to make to the chemical sensor data in a proportional manner. In some embodiments, the baseline values can be from evaluating fluid state data for the particular patient into which the device or system is implanted. In other embodiments, the baseline values can be from evaluating fluid state data for a class of similar patients (such as one or more of age, sex, diagnosis, disease progression, etc.).

In some embodiments, correcting the native or raw data can be performed by applying a function that is derived through analysis of a training set of data. The training set of data can come from the particular patient into which the device or system is implanted or from other patients, such as other similar patients. In one approach, the function can be derived by first observing the relationship between fluid state change and chemical sensor data change by having the patient, or a class of patients, assume various activity levels, postures, and/or respiration levels and observing the resulting chemical sensor values. Many different techniques can be used. In some embodiments, a best-fit algorithm can be used to derive a function that describes the relationship between changes in fluid state sensor data and chemical sensor data. Once such a function is derived, it can be used to generate normalized or corrected chemical sensor data based upon raw chemical sensor data and fluid state sensor data input.

In some embodiments, normalizing the native or raw data can be performed by matching the fluid state sensor data to a corresponding template providing specific procedures for the correction chemical sensor data and then following such procedures. By way of example, in some embodiments, the device or system can include templates corresponding to different specific fluid state sensor values. By way of example, for posture such templates can include a recumbent posture template and an upright posture template (many other postures can also be used such as fully supine, prone, right lateral recumbent, left lateral recumbent, Fowler's position, or Trendelenberg position and the like). For activity, such templates can include a resting activity template, a moderate activity template, and a high activity template (and in some embodiments intermediates thereof). Other activity templates may include muscle involvement from isometric activity such as yoga, isometric exercises or first clenching. For respiration, such templates can include a below normal respiration rate template, a normal respiration rate template, and an above normal respiration rate template (amongst many other possibilities). Other respiration templates involve pathophysiological respiratory patterns or conditions such as templates for apnea, hypopnea, hyperpnea, tachypnea, dyspnea, Cheyne-Stokes respiration and hyperventilation. Yet other respiration templates can be used for physiological but infrequent respiration patterns such as those associated with crying. After matching the fluid state sensor data to a corresponding template, the specific procedures described by the same can be executed in order to generate normalized or corrected chemical sensor data.

In some embodiments, normalizing the native or raw data can be performed by calculating a weighted-average value for the chemical sensor data. By way of example, values for the chemical sensor data corresponding to times when the fluid state is at a normal level can be weighted more heavily. Values for the chemical sensor data corresponding to times when the fluid state deviates from a normal level can be weighted less or not considered at all.

In some embodiments, rather than modifying the raw values from the chemical sensor, when the fluid state sensor data indicates a particular fluid state that may cause the chemical sensor data to be unreliable, such chemical sensor data can be omitted, ignored, discarded, or otherwise devalued. As such, in some aspects, normalization of data can include discarding or otherwise not acting upon native or raw data provided by a chemical sensor corresponding to times when the fluid state sensor data indicates that the fluid state is not normal or otherwise within a reliable range. As an example, in some embodiments the normalization circuitry can suspend chemical sensor data collection for predetermined postures, predetermined activity values, or predetermined respiration values. In some embodiments the normalization circuitry will not use or will omit chemical sensor data for predetermined postures, predetermined activity values, or predetermined respiration values. In some embodiments, the normalization circuitry will suspend chemical sensor data collection or not use the chemical sensor data for a predetermined length of time after a posture change, activity level change, or respiration change. In some embodiments, chemical sensor data is stored and/or displayed based on corresponding posture data, corresponding activity data, and/or corresponding respiration data.

In some embodiments, the normalization circuitry can categorize chemical sensor data based on the corresponding fluid state sensor data. Categorization can occur in conjunction with other normalization steps described herein. Such categorized chemical sensor data can also be displayed so as to indicate the categorization. An example of categories for posture data, activity data, and respiration data is shown below in Table 1. Many other categorizations of posture, activity and respiration are contemplated herein. In some embodiments, fluid state measures (including, but not limited to posture, activity and respiration can include from 2 to 10, or more categories. In some embodiments, the number of categories used is different for different fluid state measures.

TABLE 1

| POSTURE | ACTIVITY | RESPIRATION |
| --- | --- | --- |
| Fully Recumbent | Below Average | Below Average |
| Partially Recumbent | Average | Average |
| Upright | Above Average | Above Average |

In some embodiments, the normalization circuitry can affect how alerts are issued by the device or system, or by how an external system interprets the chemical sensor data for purposes of issuing alerts. It will be appreciated that in various embodiments, the device or system can be configured to issue an alert (which could show up on a external interface device or could pass through a data network to a remote patient management system). The alert can regard the levels of physiological analytes measured by the chemical sensor(s). However, in some embodiments, the issuance of an alert can be dependent on the fluid state corresponding to the chemical sensor data. In some embodiments, the issuance of an alert can also include data regarding the fluid state such that the alert can be acted upon or not in consideration of the corresponding fluid state data.

As an example, a system can be configured to issue alerts for potassium levels that are too high (hyperkalemia alerts) and/or alerts for potassium levels that are too low (hypokalemia alerts). Similarly, the system can be configured to issue alerts for other physiological analyte levels that are too high (hyper alerts) and/or alerts for analyte levels that are too low (hypo alerts). In some embodiments, normalization can include selecting appropriate ranges and/or threshold values (from preselected values or determined dynamically) for physiological analytes based on the patient's fluid state.

At least some of the fluid causing blood analyte concentration changes is due to movement of interstitial fluid. Therefore the effects of posture or other fluid state parameters on sensors measuring an analyte at one location may be different than the effects of posture on sensors measuring an analyte at another location. In an embodiment the same normalization is used for a sensor measuring an analyte regardless of its location within or on the body. In another embodiment different normalization is used for a first sensor measuring an analyte at a first location within or on the body than for a second sensor measuring an analyte at a second location within or on the body. Examples of a first/second locations: within blood/within interstitial fluid, in or on the thorax/in or on a leg, in an artery/in a vein, in fluid/in solid tissue.

Display and Storage

In an embodiment sensor data is categorized, stored and/or displayed based on the corresponding fluid state sensor data. In another embodiment alert threshold and ranges are categorized and displayed based on the corresponding fluid state sensor data. In one embodiment data may be categorized and displayed in a chart format, for example, a line chart, a histogram, a bar chart, a pie chart or a bubble chart or any combination of these charts. In another embodiment data may be categorized and displayed in a table.

Figure 8:
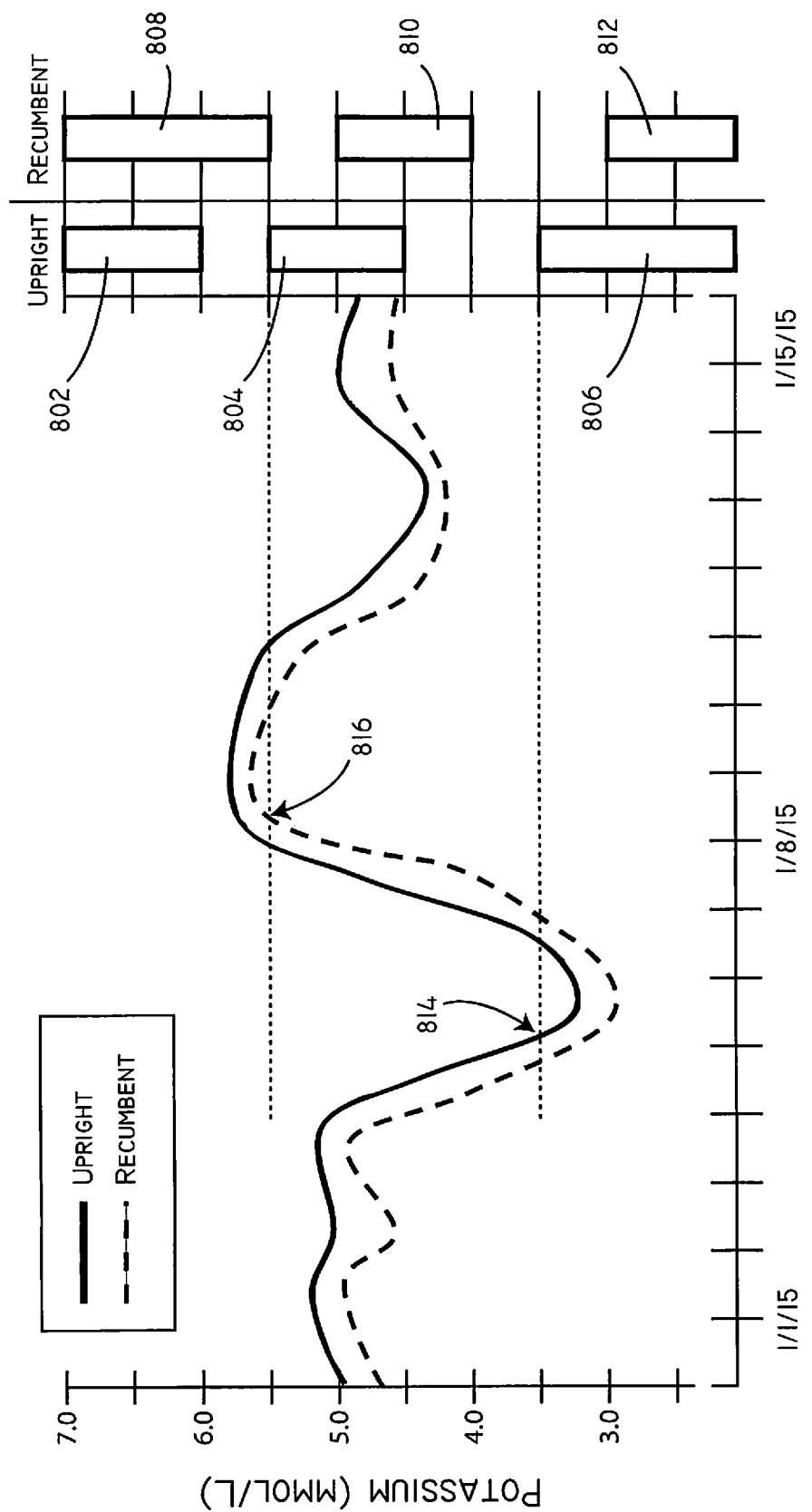
FIG. 8 is a combined line chart and bar chart showing exemplary chemical sensor data for potassium concentrations over time as measured at upright and recumbent postures.

Referring now to FIG. 8, a combined a line chart and bar chart is shown of exemplary chemical sensor data for potassium concentrations over time as measured at upright and recumbent postures. As can be seen, the potassium concentrations measured during recumbency are generally lower than as measured in an upright posture. In this example, there is a hyper range 802 (or hyper threshold when considering the bottom limit thereof), a target range 804, and a hypo range 806 (or hypo threshold when considering the top limit thereof) corresponding to measurements taken when the fluid state is an upright posture. There is also a hyper range 808 (or hyper threshold when considering the bottom limit thereof), a target range 810, and a hypo range 812 (or hypo threshold when considering the top limit thereof) corresponding to measurements taken when the fluid state is a recumbent posture. The recumbent hyper, target, and hypo ranges are offset lower as compared with the corresponding upright posture ranges. As such, it can be seen that as an alternative to (or in combination with) effectively changing the chemical sensor values based on the fluid state, the normalization circuitry can also shift the threshold values or ranges that are used for issuing alerts, initiating or controlling therapy, or for other purposes. At time point 814, the potassium amount falls below the hypo threshold for potassium as evaluated with the patient in an upright posture and a hypo alert can be issued or otherwise triggered. At time point 816, the potassium amount climbs above the hyper threshold for potassium as evaluated with the patient in a recumbent posture and a hyper alert can be issued or otherwise triggered. While FIG. 8 shows two different categories for posture as a fluid state component, it will be appreciated that there can be more than two categories, such as 3, 4, 5, 6, 7, 8 or more categories. In addition, while FIG. 8 shows categories specific for posture, it will be appreciated that the example could also be illustrated with other fluid state aspects such as respiration, activity, or other fluid state measures. Further, although FIG. 8 pertains to potassium, it will be appreciated that similar methods can be applied to other analytes.

In various approaches to normalization, the fluid state corresponding to particular chemical sensor data is evaluated. In some embodiments, this means that fluid state sensor data from the same time or time period as the chemical sensor data is used (e.g., corresponding means simultaneous time or time period). However, in some embodiments, the time between the fluid state data and the chemical sensor data for purposes of what corresponds is offset. By way of example, while changing posture can, in many cases, have an effect on chemical sensor data, in some cases the effect may be offset in time from the posture (or other fluid state) change (e.g., there can be a latency). By way of example, if the posture change occurs at time "0", then the chemical sensor data may not be impacted by the fluid state change unit time "0" plus 5 minutes. As such, in some embodiments the fluid state data that corresponds to particular chemical sensor data is offset to account for latency by at least 15 seconds, 30 seconds, 45 seconds, 1 minute, 2 minutes, 3 minutes, 4 minutes, 5 minutes, 10 minutes, 15 minutes, 20 minutes, 30 minutes, or more. In some embodiments the fluid state data that corresponds to particular chemical sensor data is offset by less than 120 minutes, 90 minutes, 60 minutes, 45 minutes, 30 minutes, 20 minutes, 15 minutes, 10 minutes, 5 minutes, 4 minutes, 3 minutes, 2 minutes, or 1 minute, or less.

Methods

Figure 9:
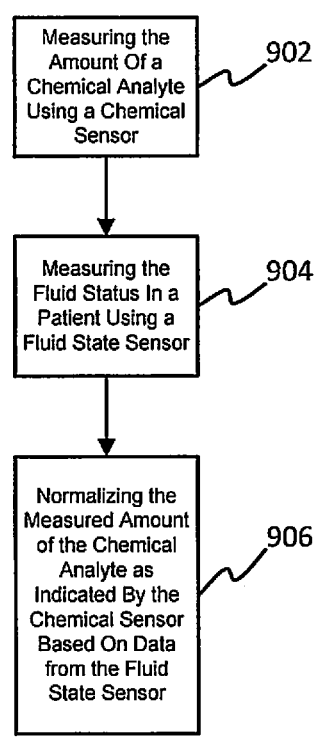
FIG. 9 is a flowchart showing operations that can be performed in accordance with various embodiments herein.

Embodiments herein can include various methods. Exemplary methods can include any of the approaches and/or operations described above. In an embodiment, a method for operating an implantable medical device system is included. Referring now to FIG. 9, the method can include operations of measuring the amount of a chemical analyte using a chemical sensor 902, measuring the fluid status in a patient using a fluid state sensor 904, and normalizing the measured amount of the chemical analyte as indicated by the chemical sensor using normalization circuitry based on data from the fluid state sensor 906. In particular, normalizing operations can include any of the approaches and/or operations described above.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like. "Circuitry" can include both hardwired circuitry for execution of particular operations as well as processors that are programmed to execute instructions to provide the same functionality.

All publications and patent applications in this specification are indicative of the level of ordinary skill in the art to which this specification pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. An implantable medical device system comprising:
   a chemical sensor configured to generate chemical sensor data;
   a fluid state sensor, the fluid state sensor comprising a posture sensor configured to generate fluid state sensor data to differentiate between patient postures, the fluid state sensor data corresponding to patient postures comprising at least an upright posture and a recumbent posture; and
   normalization circuitry configured to receive the chemical sensor data and the fluid state sensor data and normalize the chemical sensor data based on the patient postures comprising at least an upright posture and a recumbent posture corresponding to the fluid state sensor data; and
   wherein the normalization circuitry is further configured to categorize the chemical sensor data based on the patient postures comprising at least an upright posture and a recumbent posture corresponding to the fluid state sensor data.

2. The implantable medical device system of claim 1, the normalization circuitry discarding chemical sensor data, ignoring chemical sensor data, or suspending chemical sensor data collection when the fluid state sensor data indicates a fluid state exceeding a threshold value.

3. The implantable medical device system of claim 1, the normalization circuitry labeling data coming from the chemical sensor based on the patient postures corresponding to the fluid state sensor data.

4. The implantable medical device system of claim 1, wherein the categorization of chemical sensor data based on the patient postures comprising at least an upright posture and a recumbent posture corresponding to the fluid state sensor data further comprises categorizing the chemical sensor data into one or more categories comprising a fully recumbent posture or a partially recumbent posture.

5. The implantable medical device system of claim 4, the normalization circuitry adjusting alert and/or therapy thresholds according to the category.

6. The implantable medical device system of claim 4, the normalization circuitry adjusting the chemical sensor data according to the category.

7. The implantable medical device system of claim 1, wherein the normalization circuitry matches fluid state sensor data with chemical sensor data that is offset in time from one another.

8. The implantable medical device system of claim 1, wherein the normalization circuitry uses fluid state sensor data from an earlier time to process chemical sensor data from a later time.

9. The implantable medical device system of claim 1, the normalization circuitry matching a measured fluid state as determined by the fluid state sensor data to a template for that fluid state.

10. The implantable medical device system of claim 9, the normalization circuitry further adjusting the chemical sensor values according to the template.

11. The implantable medical device system of claim 1, the normalization circuitry calculating a weighted average for the chemical sensor data with the weight based on the fluid state sensor data.

12. The implantable medical device system of claim 1, the chemical sensor data comprising native values for amounts of a measured physiological analyte;
   the normalization circuitry generating a normalized value by
   increasing the native value when a fluid state sensor measured value indicates that the measured physiological analyte has been decreased; and
   decreasing the native value when a fluid state sensor measured value indicates that the measured physiological analyte has been increased.

13. The implantable medical device system of claim 1, further comprising therapy control circuitry controlling parameters of a therapy delivery to a patient; the therapy control circuitry to omit changes in physiological analyte concentrations from consideration when the normalization circuitry indicates that current chemical sensor data is unreliable.

14. The implantable medical device system of claim 1, further comprising recorder circuitry to record the data produced by the chemical sensor and/or the fluid state sensor and time stamps regarding the same.

15. The implantable medical device system of claim 1, the normalization circuitry producing normalized chemical sensor data; the system further comprising recording circuitry to record the normalized chemical sensor data and time stamps regarding the same.

16. An implantable medical device system comprising:
   a chemical sensor;
   a fluid state sensor comprising
      a posture sensor configured to generate fluid state sensor data used to differentiate between patient postures, the fluid state sensor data corresponding to patient postures comprising at least an upright posture and a recumbent posture; and
   an external interface device configured to communicate with the implantable medical device;
   the external interface device including a processor configured to receive data from the chemical sensor and the fluid state sensor and normalize the chemical sensor data based on the patient postures comprising at least an upright posture and a recumbent posture corresponding to the fluid state sensor data; and
   wherein the processor is further configured to categorize the chemical sensor data based on the patient postures comprising at least an upright posture and a recumbent posture corresponding to the fluid state sensor data.

17. A method of operating an implantable medical device system comprising:
   measuring the amount of a chemical analyte using a chemical sensor;
   normalizing the measured amount of the chemical analyte as indicated by the chemical sensor using normalization circuitry based on the patient postures comprising at least an upright posture and a recumbent posture corresponding to the posture sensor data; and
   categorizing the chemical sensor data based on the patient postures comprising at least an upright posture and a recumbent posture corresponding posture sensor data.

18. The implantable medical device system of claim 1, wherein the posture sensor comprises an accelerometer configured to detect a posture that is vertically or horizontally oriented; or an impedance sensor configured to measure a trans-thoracic or vessel impedance to determine the patient's posture.

19. The implantable medical device system of claim 1, wherein the normalization circuitry is further configured to shift one or more threshold values or one or more ranges, for issuing an alert, initiating a therapy, or controlling a therapy based on the fluid state data.

* * * * *